United States Patent
Wilson et al.

(10) Patent No.: US 12,245,961 B2
(45) Date of Patent: Mar. 11, 2025

(54) GUIDE CATHETER FOR FLOW MODIFYING DEVICE

(71) Applicant: Shockwave Medical, Inc., Santa Clara, CA (US)

(72) Inventors: Scott R. Wilson, Maple Grove, MN (US); Sai Ho Choy, Richmond (CA); Keith Alan Jackson, Newberry, FL (US); Ernest Wai Wong, Douglaston, NY (US); Guy Patrick Vanney, Blaine, MN (US); Jason Lee Ladoucer, North Branch, MN (US); Fredericus Antonius Colen, Ponte Vedra Beach, FL (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 136 days.

(21) Appl. No.: 17/983,869

(22) Filed: Nov. 9, 2022

(65) Prior Publication Data

US 2024/0058586 A1    Feb. 22, 2024

Related U.S. Application Data

(63) Continuation of application No. PCT/US2022/040932, filed on Aug. 19, 2022.

(51) Int. Cl.
*A61F 2/966* (2013.01)
*A61B 17/12* (2006.01)
(Continued)

(52) U.S. Cl.
CPC ........ *A61F 2/966* (2013.01); *A61B 17/12122* (2013.01); *A61F 2/95* (2013.01);
(Continued)

(58) Field of Classification Search
None
See application file for complete search history.

(56) References Cited

U.S. PATENT DOCUMENTS

| 5,306,263 A | 4/1994 | Voda |
| 5,573,520 A | 11/1996 | Schwartz et al. |

(Continued)

FOREIGN PATENT DOCUMENTS

| CN | 215961743 U | 3/2022 |
| EP | 1360972 A1 | 11/2003 |

(Continued)

OTHER PUBLICATIONS

"U.S. Appl. No. 17/924,254 Preliminary Amendment Filed with Application", 9 pages.

(Continued)

*Primary Examiner* — Rebecca S Preston
(74) *Attorney, Agent, or Firm* — Morrison & Foerster LLP

(57) ABSTRACT

A system for implanting a flow modifying device in a heart comprises a flow modifying device comprising a tubular body comprising first and second openings located at first and second ends of the tubular body and a neck positioned between the first opening and the second opening, and a guide catheter comprising a flexible elongate shaft comprising a proximal portion comprising a fitting for receiving an insertion instrument and distal portion comprising an enlarged distal tip to prevent the flexible elongate shaft from passing through the flow modifying device. A guide catheter for cannulating a coronary sinus from a superior vena cava comprises a pre-formed distal portion comprising a proximal straight zone, a proximal curved zone extending along a first curved path, a distal straight zone extending along a straight path and a distal curved zone extending along a second (Continued)

curved path. The guide catheter can have different stiffnesses.

17 Claims, 19 Drawing Sheets

(51) Int. Cl.
*A61F 2/95* (2013.01)
*A61F 2/958* (2013.01)
*A61M 25/01* (2006.01)
*A61M 25/10* (2013.01)
*A61M 25/00* (2006.01)

(52) U.S. Cl.
CPC ............ *A61F 2/958* (2013.01); *A61M 25/01* (2013.01); *A61M 25/10* (2013.01); *A61B 2017/1205* (2013.01); *A61B 17/12109* (2013.01); *A61F 2230/001* (2013.01); *A61F 2250/0013* (2013.01); *A61F 2250/0039* (2013.01); *A61F 2250/0098* (2013.01); *A61M 25/0053* (2013.01)

(56) References Cited

U.S. PATENT DOCUMENTS

| | | | |
|---|---|---|---|
| 5,618,301 | A | 4/1997 | Hauenstein et al. |
| 5,701,905 | A | 12/1997 | Esch |
| 5,811,043 | A | 9/1998 | Horrigan et al. |
| 5,814,027 | A | 9/1998 | Hassett et al. |
| 5,814,029 | A | 9/1998 | Hassett |
| 6,612,999 | B2 | 9/2003 | Brennan et al. |
| 6,945,956 | B2 | 9/2005 | Waldhauser et al. |
| 7,128,956 | B2 | 10/2006 | Wang et al. |
| 7,542,808 | B1 | 6/2009 | Peterson et al. |
| 7,556,625 | B2 | 7/2009 | Johnson |
| 7,942,865 | B2 | 5/2011 | Johnson |
| 7,993,351 | B2 | 8/2011 | Worley et al. |
| 9,636,173 | B2 | 5/2017 | Goshgarian et al. |
| 10,518,065 | B2 | 12/2019 | Linden et al. |
| 10,588,611 | B2 * | 3/2020 | Magnin ............ A61B 17/00234 |
| 2004/0220521 | A1 | 11/2004 | Barbut |
| 2009/0182412 | A1 * | 7/2009 | Tan .................... A61F 2/966 |
| | | | 604/509 |
| 2012/0035700 | A1 * | 2/2012 | Leanna ................. A61F 2/95 |
| | | | 623/1.11 |
| 2013/0158653 | A1 | 6/2013 | Gamarra et al. |
| 2020/0178978 | A1 | 6/2020 | Ben-Muvhar et al. |
| 2020/0229956 | A1 * | 7/2020 | Jackson .............. A61F 2/915 |
| 2020/0246527 | A1 | 8/2020 | Hildebrand et al. |
| 2021/0196283 | A1 * | 7/2021 | Zhang ................. A61F 2/82 |
| 2022/0203070 | A1 | 6/2022 | Okamura et al. |
| 2022/0287831 | A1 * | 9/2022 | Thornton ............ A61F 2/966 |
| 2022/0378590 | A1 * | 12/2022 | Knoepp .............. A61F 2/06 |
| 2023/0076384 | A1 * | 3/2023 | Cummings .......... A61F 2/2436 |

FOREIGN PATENT DOCUMENTS

| | | | |
|---|---|---|---|
| EP | 2465568 | A1 | 6/2012 |
| WO | WO-2002030310 | A1 | 4/2002 |
| WO | WO-2009137712 | A1 | 11/2009 |

OTHER PUBLICATIONS

"International Application Serial No. PCT/US2022/040932, International Search Report mailed Jan. 25, 2023", 4 pgs.
"International Application Serial No. PCT/US2022/040932, Invitation to Pay Additional Fees mailed Nov. 10, 2022", 2 pgs.
"International Application Serial No. PCT/US2022/040932, Written Opinion mailed Jan. 25, 2023", 10 pgs.
Beck, C S, et al., "The Surgical Management of Coronary Artery Disease: Background, Rationale, Clinical Experiences", American College of Physicians in Annals of Internal Medicine, Ann Intern Med. 45(6), (Dec. 1956), 14 pgs.
Brofman, B. L., "Long Term Influence of the Beck Operation for Coronary Heart Disease", American Journal of Cardiology, 6, (Aug. 1960), 259-271.
Extended European Search Report received for European Patent Application No. 23158644.7, mailed on Jan. 22, 2024, 7 pages.
Extended European Search Report received for European Patent Application No. 23158647.0, mailed on Jan. 3, 2024, 7 pages.

* cited by examiner

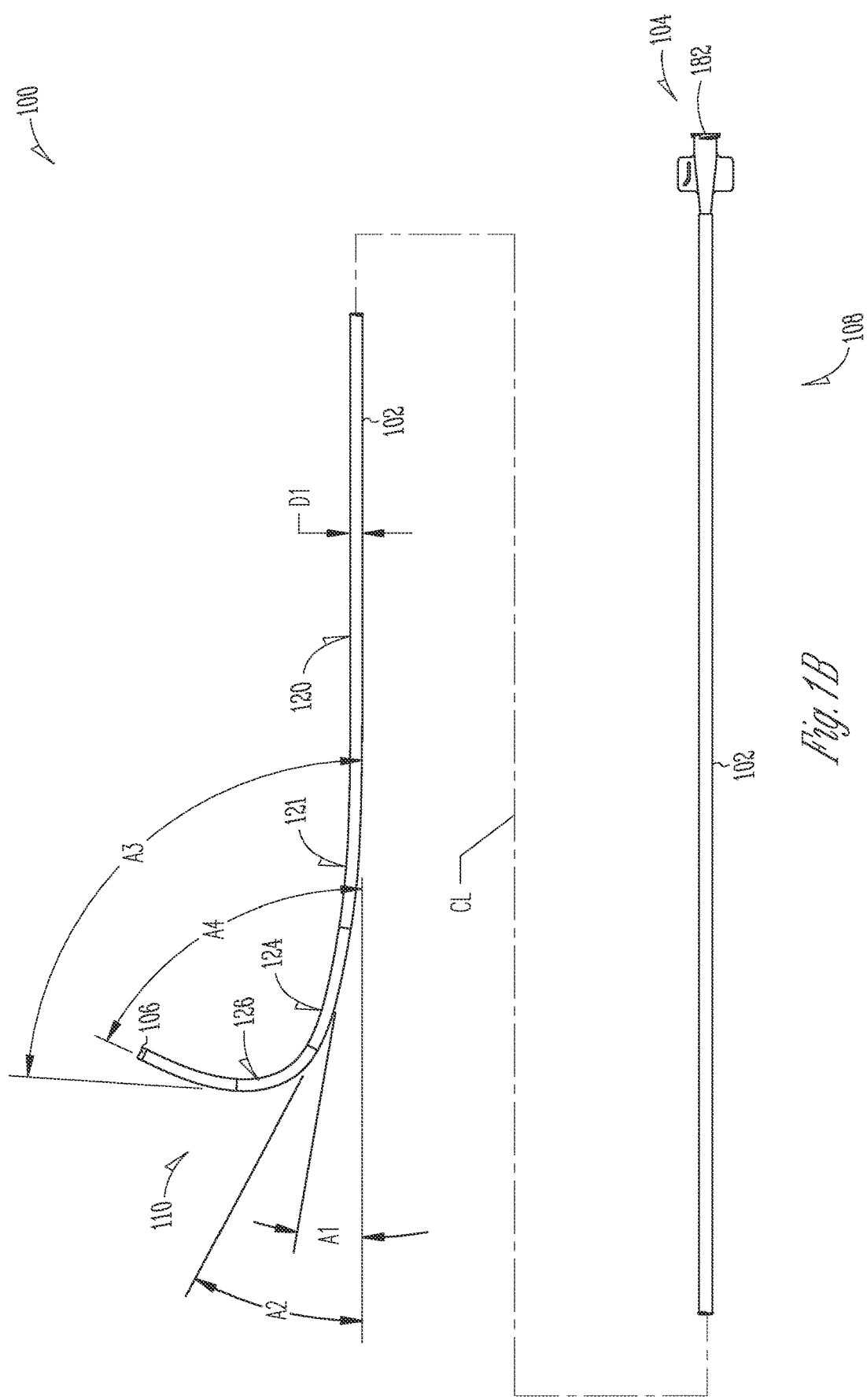

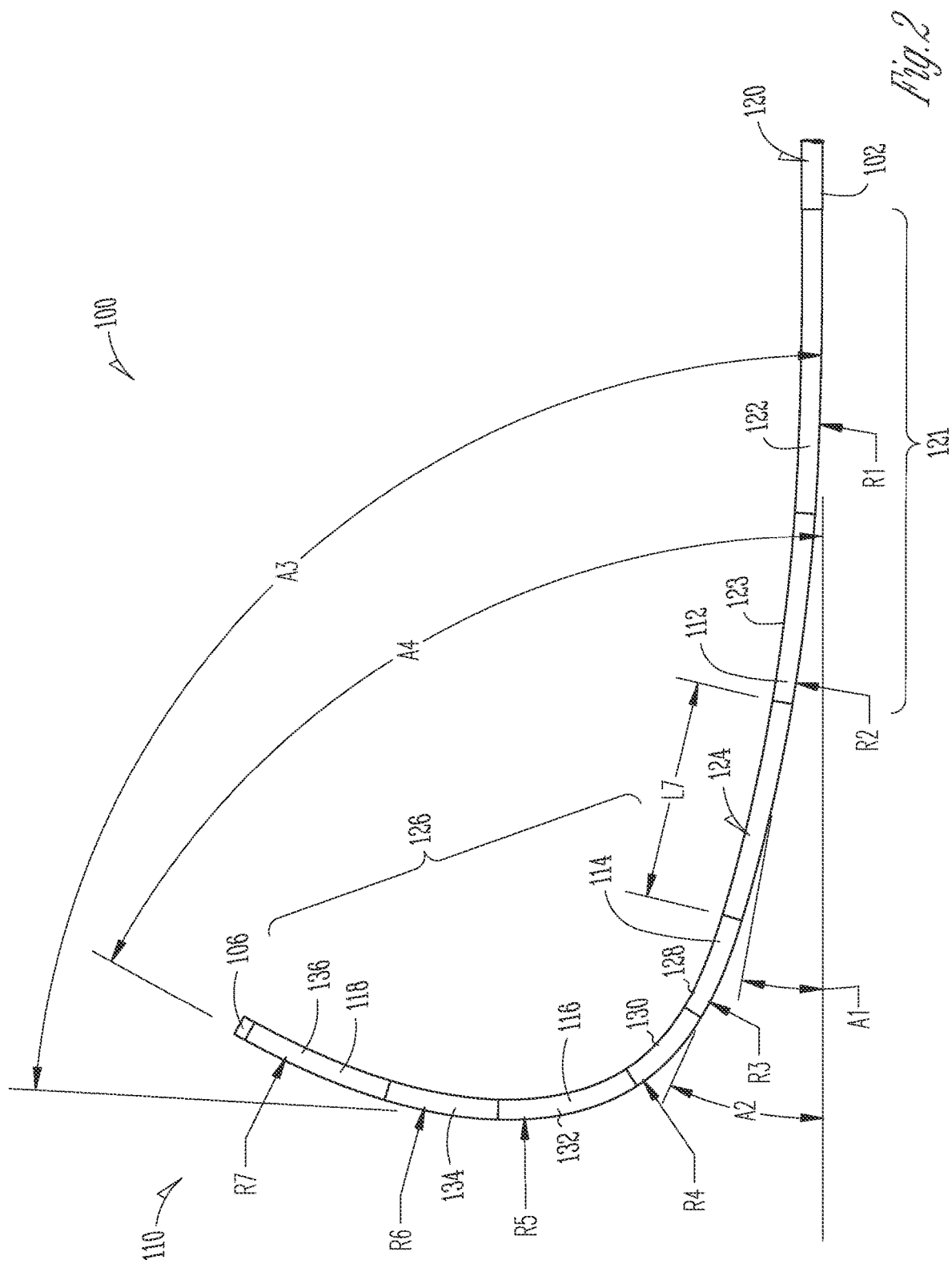

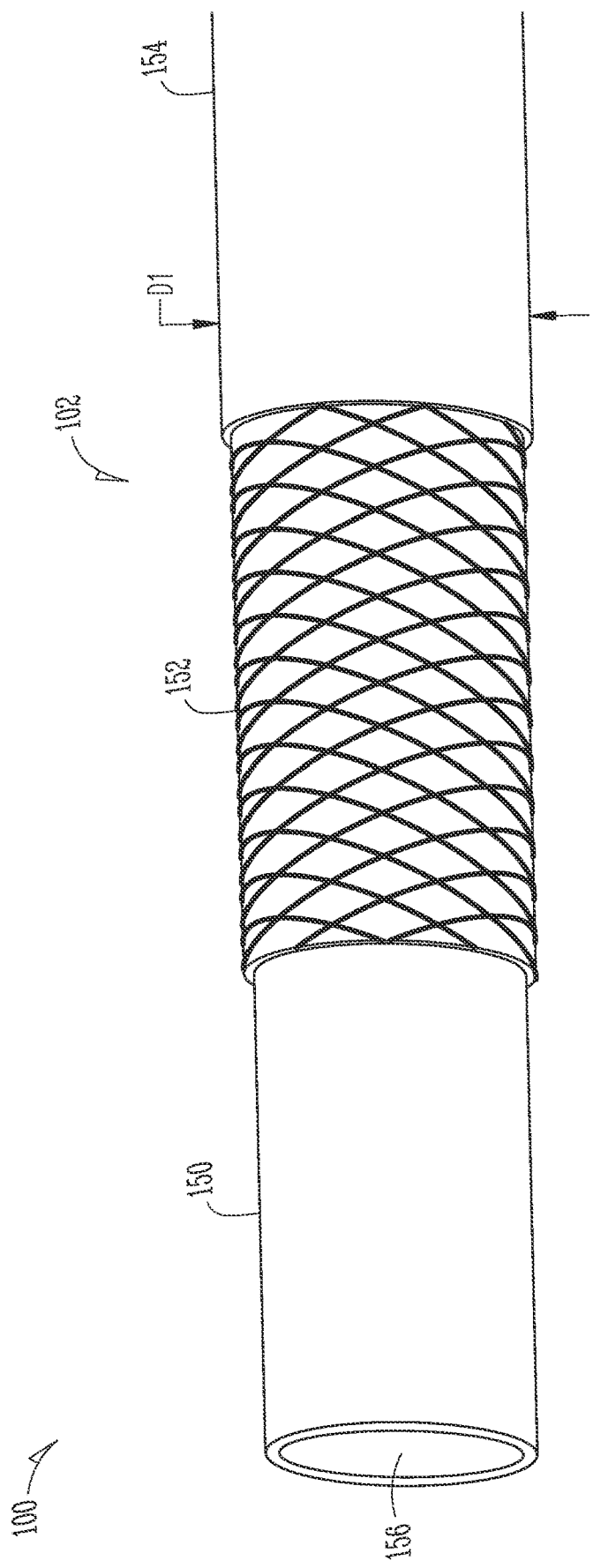

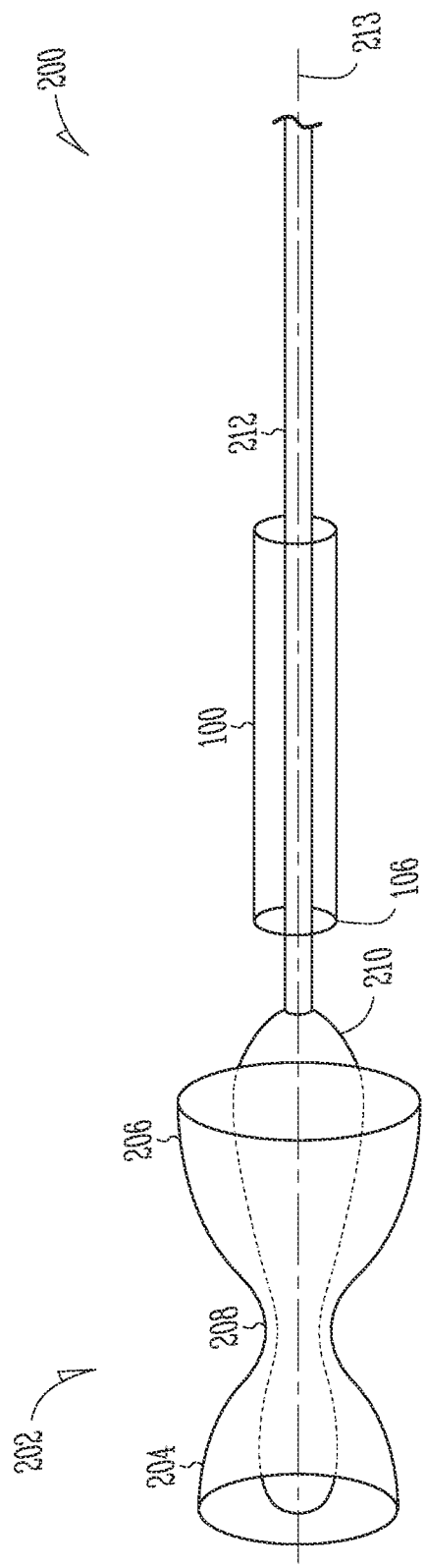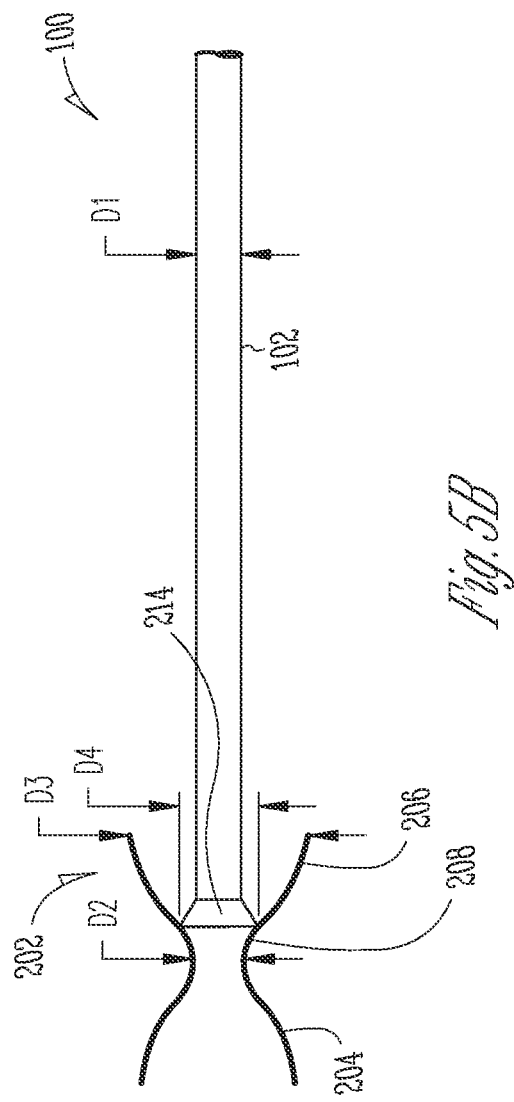
Fig. 5A
Fig. 5B

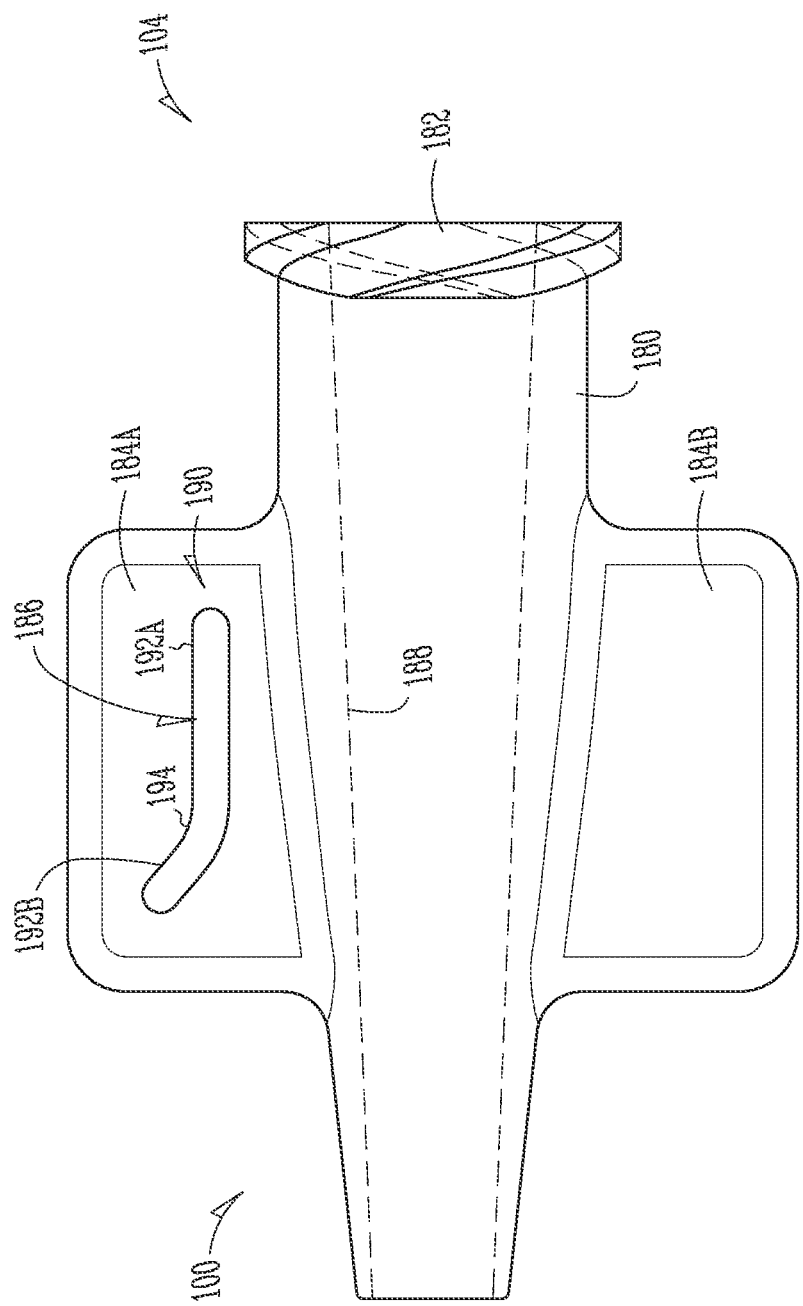

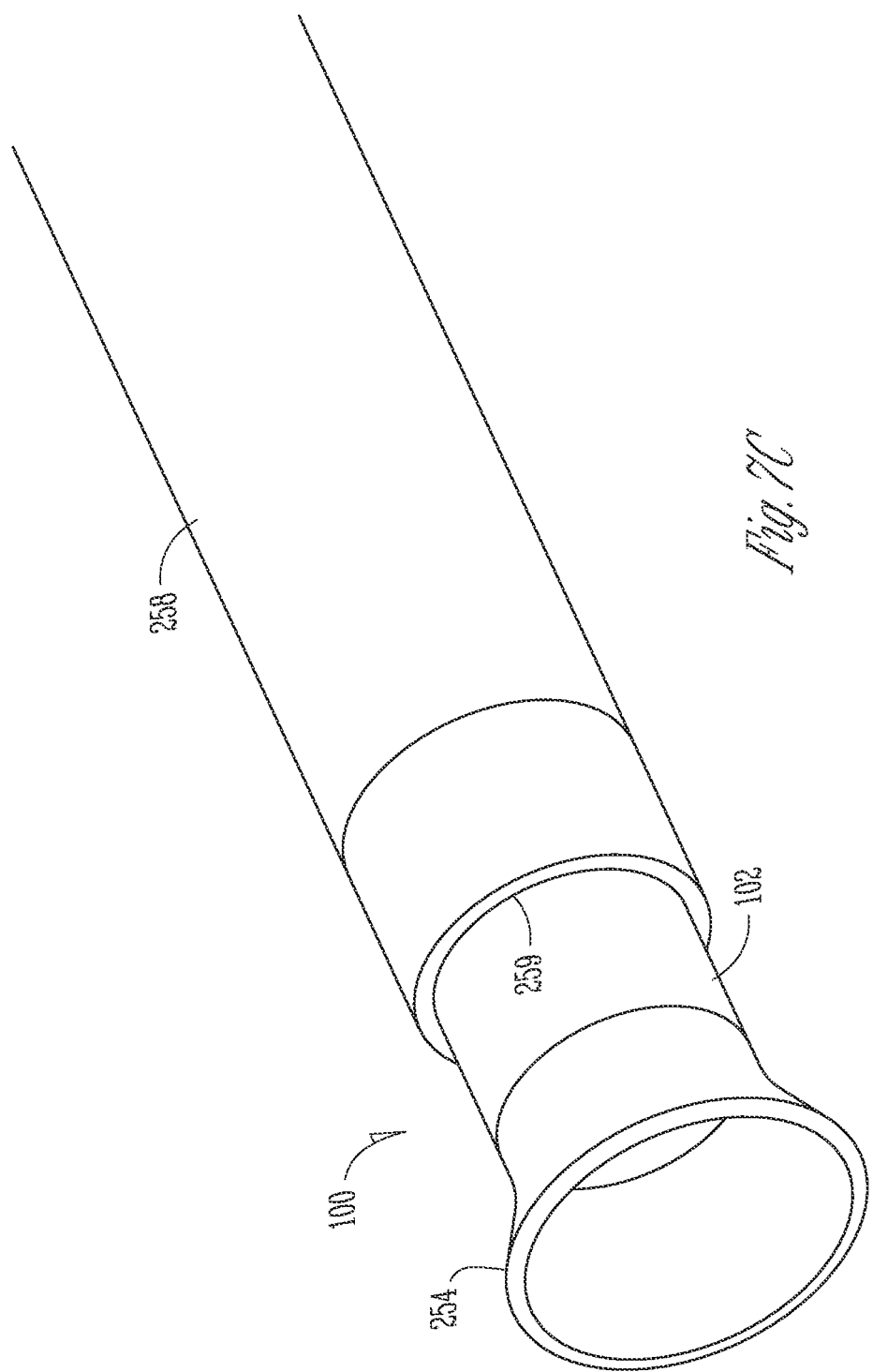

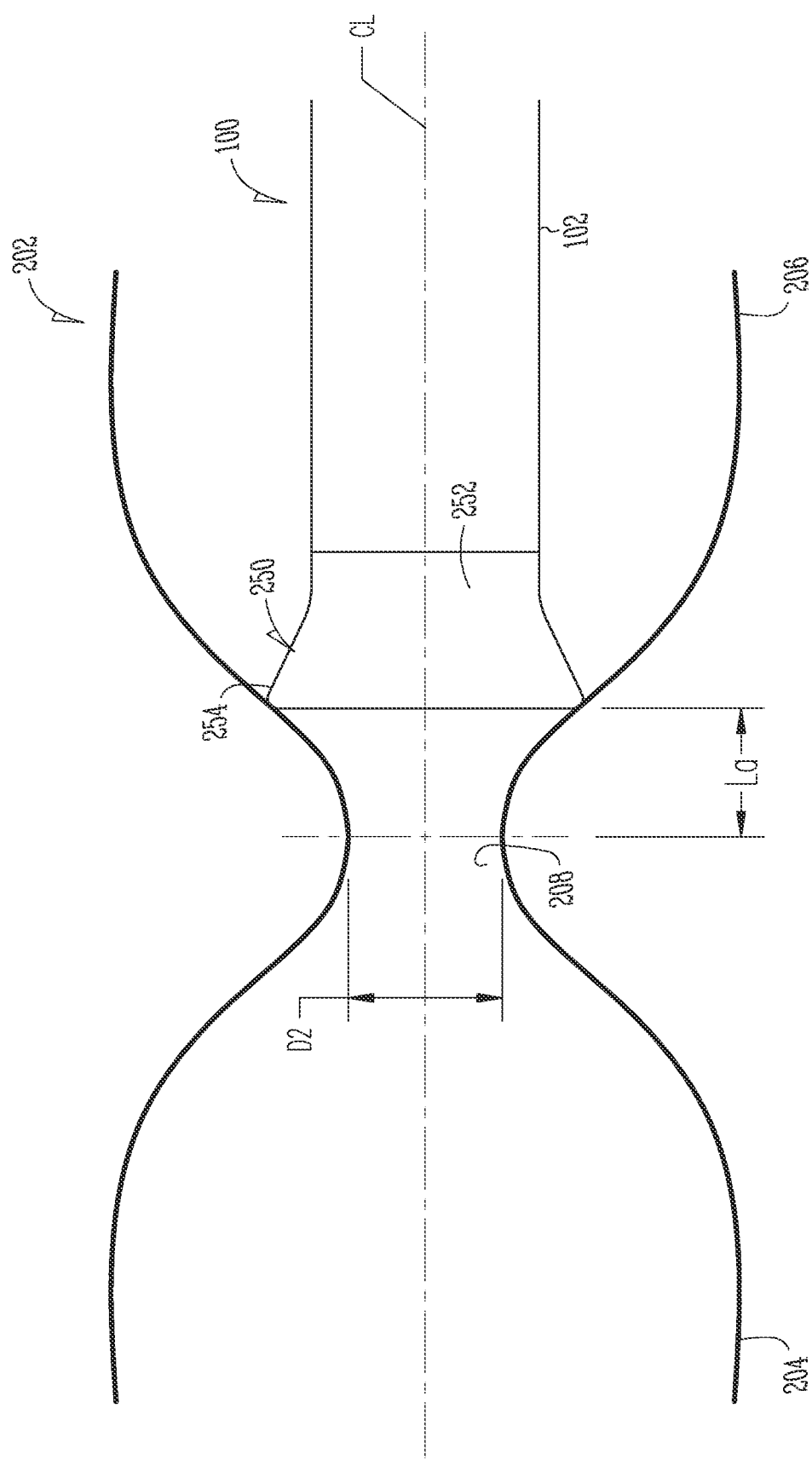

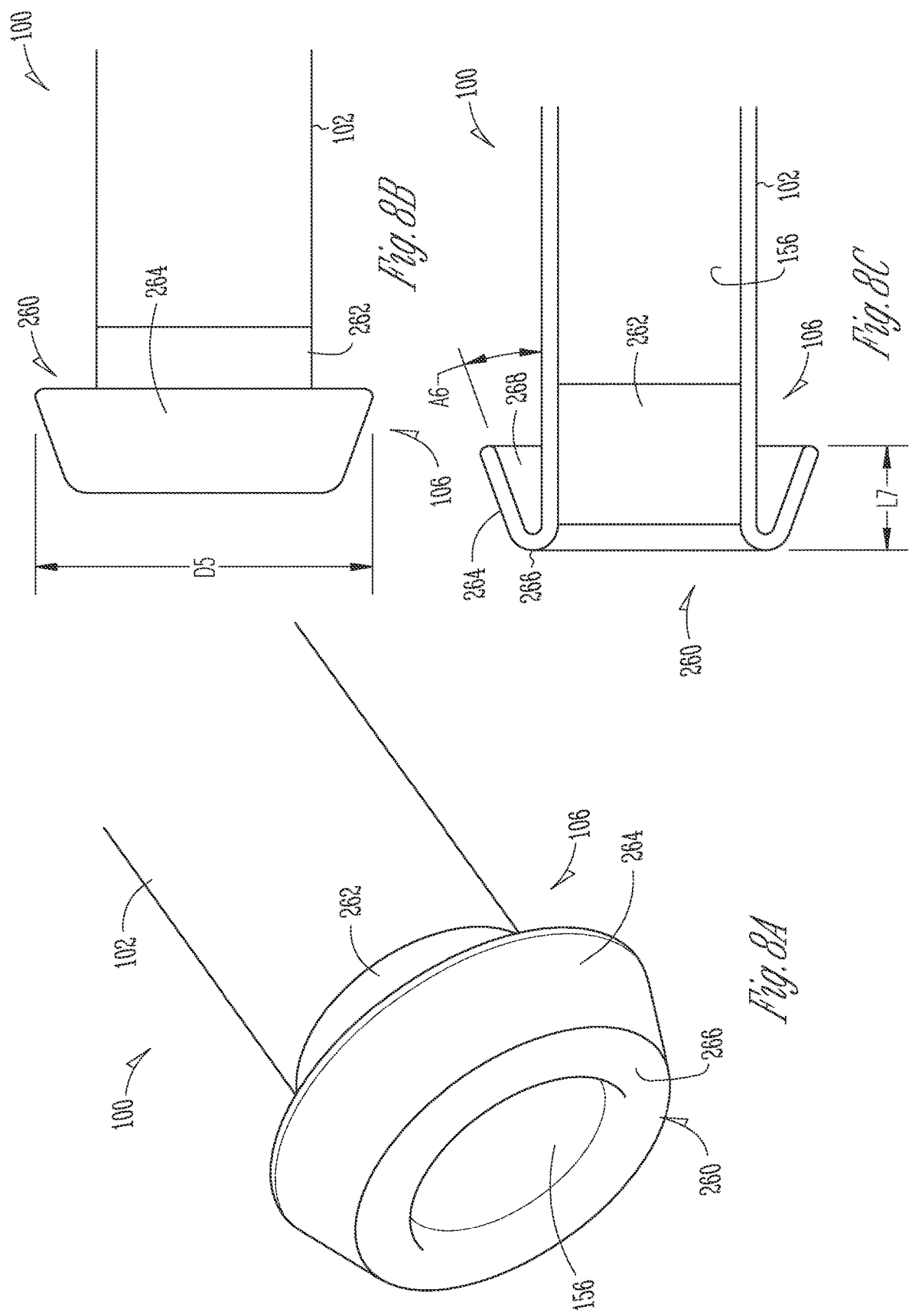

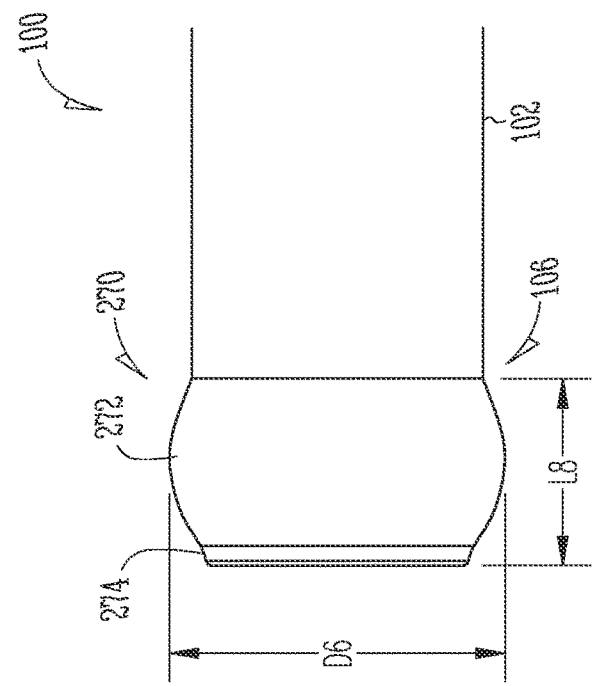
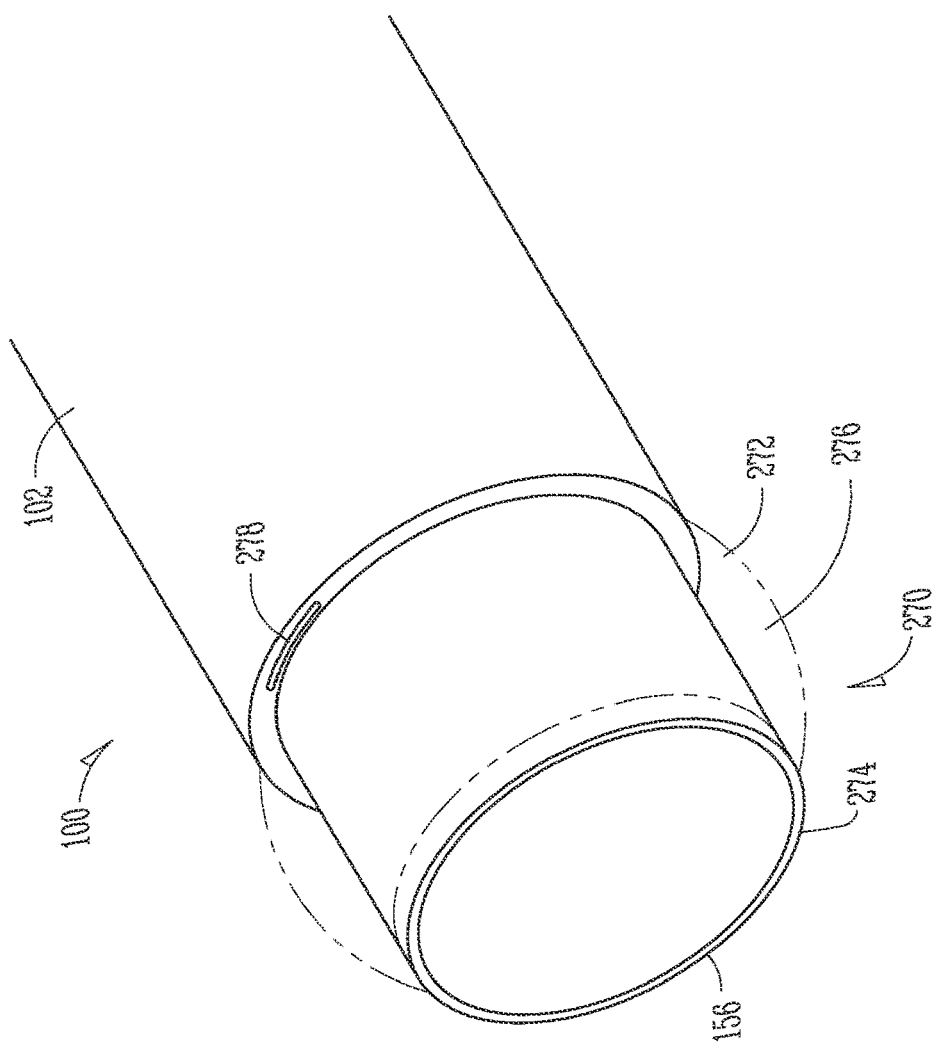
Fig. 9B
Fig. 9A

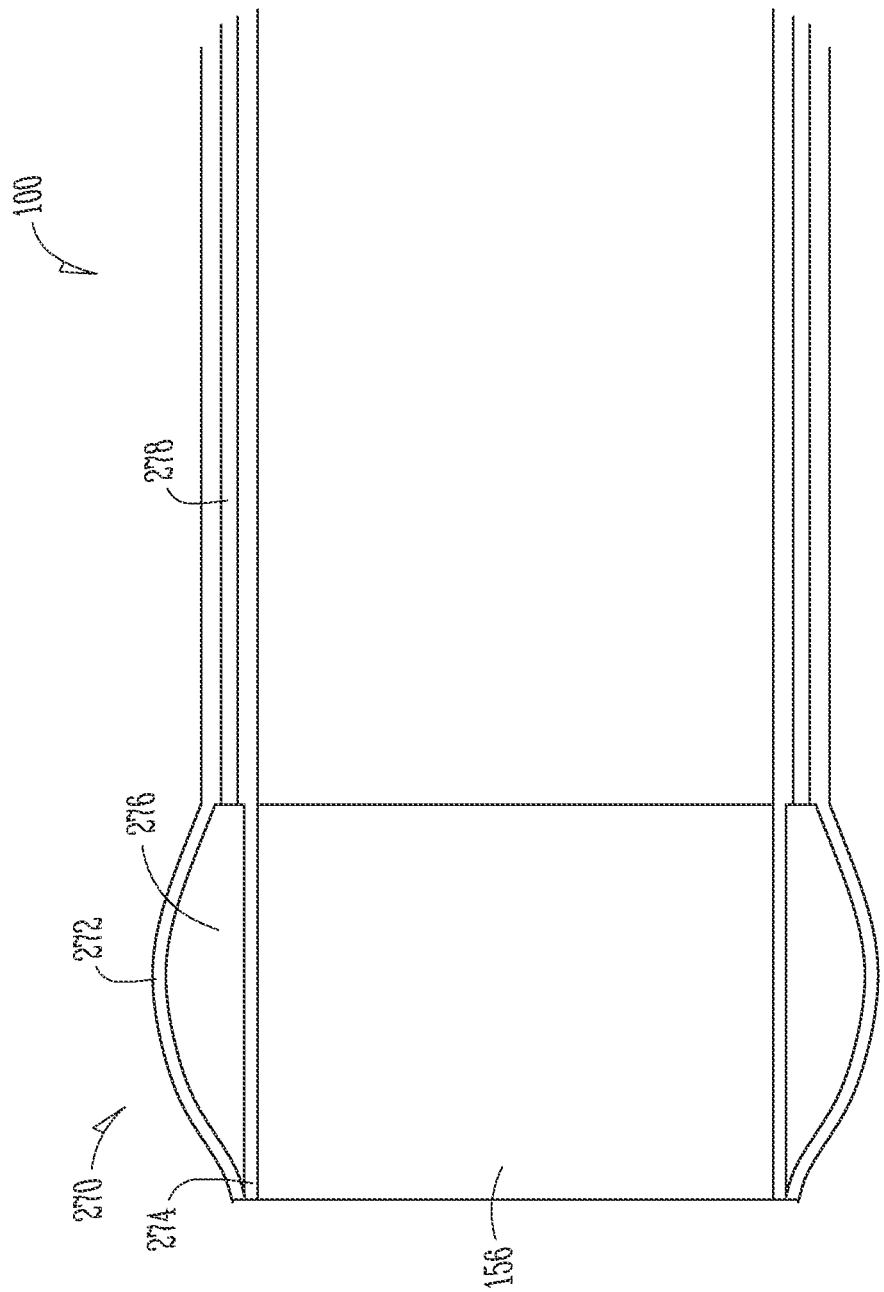

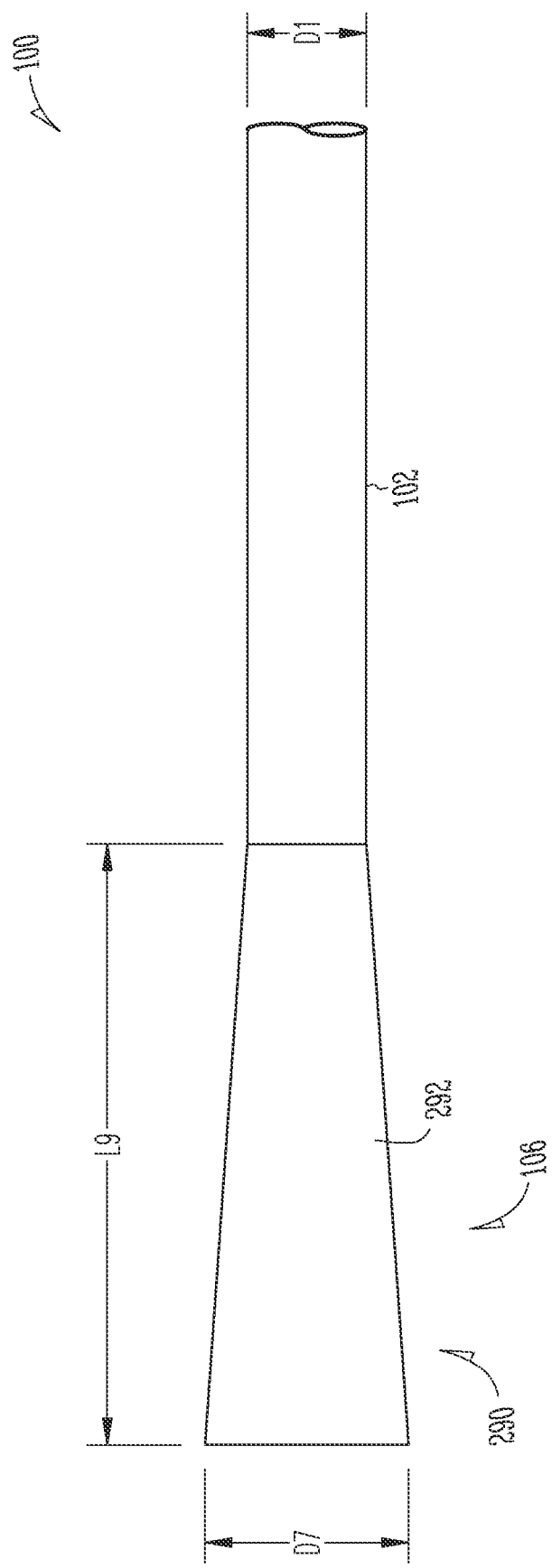

GUIDE CATHETER FOR FLOW MODIFYING DEVICE

CROSS-REFERENCE TO RELATED APPLICATION

This application is a continuation of International Application No. PCT/US2022/040932, filed on Aug. 19, 2022, which application is incorporated herein by reference in its entirety.

TECHNICAL FIELD

This document pertains generally, but not by way of limitation, to elongate surgical instruments configured to inserted into anatomic ducts to deliver medical devices to specific internal anatomic locations. More specifically, but not by way of limitation, the present application relates to guide catheters that can be used to deliver flow modifying devices to the heart.

BACKGROUND

The heart pumps blood through the body. The heart itself is fed by coronary arteries that end at capillaries. The capillaries are drained by a network of coronary veins, that typically flow into a vein known as the coronary sinus. The coronary sinus is a short, large diameter vein that is substantially contiguous with a right atrium, the atrium that collects all venous blood from the body.

Occlusion of coronary arteries is a leading cause of death, especially sudden death, in what is commonly called a "heart attack." When blood flow to a portion of the heart is suddenly stopped, the portion becomes ischemic and its electrical activity is disrupted. As the activity of the heart is mediated by electrical signal propagation, such disruption typically propagates to the rest of the heart, disorganizes activation of the heart and causes heart output to be reduced, in some cases drastically, which can lead to ischemia and death of the brain. In addition, the disorganized activity often damages the heart beyond what was caused directly by the blockage.

If a patient survives the direct effects of the heart attack, the damage to the heart may predispose the patient to future electrical disorders or may significantly reduce cardiac output, thus reducing quality of life and life expectancy.

Angina pectoris is a chronic or semi-chronic condition that, while not life-threatening, significantly reduces quality of life. In general, the heart responds to increased demand by working harder, requiring more coronary blood flow. When coronary arteries are stenosed or occluded, the increased blood flow cannot be provided, and pain, caused by the resulting ischemia, is produced.

The heart has natural mechanisms to overcome stenosis in coronary arteries. One such mechanism is angiogenesis, in which new arteries are created, for bypassing the stenosis.

Since angiogenesis sometimes does not occur naturally, various procedures have been suggested to encourage it. For example, Trans-Myocardial Revascularization (TMR), is a process in which multiple holes are drilled in the heart, with the intent of causing new vessels to be created.

Beck, in "The Surgical Management of Coronary Artery Disease: Background, Rationale, Clinical Experience" by C. S. Beck and B. L. Brofman, 1956, by the American College of Physicians in Annals of Internal Medicine Vol. 45, No. 6, December 1956 and in "Long Term Influence of the Beck Operation for Coronary Heart Disease", by B. L. Brofman in the American Journal of Cardiology August 1960, the disclosures of which are incorporated herein by reference, performed open chest surgery in which a coronary sinus vein was restricted, by an external suture. After a few months, coronary blood supply apparently improved. However, this method has fallen in disfavor, in part possibly due to the need to open the chest and lift up the heart, to reach the coronary sinus vein.

A standard treatment of stenosed arteries is inserting a stent into the artery, at the stenosed point. The stent, for example a metal coil or mesh, is expanded to have an inner diameter similar to that of the original stenosed blood vessel. If many or elongated stenoses are present, it is not common to implant multiple stents. Instead, a bypass procedure, in which a conduit is used to bypass the stenoses, is performed.

U.S. Pat. No. 5,618,301, the disclosure of which is incorporated herein by reference, describes a stent-like device for reducing the diameter of a body conduit. What is described is an open mesh stent that can be inserted in a channel created by a TIPS (Trans-Jugular Intra-Hepatic Portal-Systemic Shunt) procedure, to reduce the blood flow rate through the channel, in order to ensure the flow diameter is reduced and prevent flow through the open mesh, a plurality of thromobogentic threads are provided on the outside of the mesh. However, as can be appreciated, intentionally forming thrombosis in most any part of the vascular system, and especially near the heart, can lead to propagating coagulation or floating thromboses, which are potentially fatal.

Delivery of such stents and stent-like devices to various anatomic regions of the heart can be complicated. Typically, a guide catheter comprising an elongate flexible tube can be used to reach target tissue where the stent or stent-like device is to be deployed. Subsequently, a delivery device can be inserted into the guide catheter to position the stent or stent-like device at the target tissue. Guide catheters can be pre-curved to facilitate reaching the target tissue. U.S. Pat. No. 7,556,625 B2 to Johnson discloses a "Coronary sinus lead delivery catheter."

OVERVIEW

The present inventors have recognized, among other things, that problems to be solved with guide catheters include the difficulty of catheters holding their position within the anatomy once inserted into the desired position to reach the target tissue. For example, some guide catheters are pre-shaped to facilitate guidance to and positioning within a particular anatomy. However, when another insertion instrument, such as a delivery catheter for deploying an expandable flow modifying device, is inserted through the guide catheter, the tip of the guide catheter can lose its position within the anatomy, thereby becoming separated from the target tissue and making it more difficult to position the flow modifying device is the desired location.

The present subject matter can provide solutions to this problem and other problems, such as by providing a pre-shaped guide catheter that can better hold its position within anatomy while receiving a guide catheter therethrough. The pre-shaped catheter can include proximal and distal curved zoned between which is located a straight zone. Such a pre-shaped catheter can better push against anatomy, such as a coronary sinus, while receiving a delivery catheter.

The present inventors have recognized that expandable and implantable medical devices are often inserted and deployed using generic, off-the-shelf instruments, such as insertion and guide catheters that are designed to function with a wide variety of medical devices. The present inventors have recognized that the compatibility of generic implantation instrumentation with specific medical devices can lead to difficulties in the implantation procedure, which can sometimes affect the outcome. For example, sometimes the relative sizing of guide catheters can result in guide catheters being undesirably inserted into a medical device or difficulty in retracting deployment balloons back into the guide catheter. These issues can lead to difficulties in positioning and shaping the implantable medical device.

The present subject matter can provide solutions to these and other problems by providing implantation instrumentation such as guide catheters specifically shaped and sized to function with specific implantable medical devices. For example, the present disclosure describes a guide catheter having a shaped tip designed to engage with specific implantable medical devices. e.g., a flow modifying device, in a particular manner. The shaped tips can be enlarged relative to a shaft of the guide catheter to prevent the guide catheter from passing through the implantable medical device. The shaped tip can engage the implantable medical device in a flush manner over a larger surface area, as compared to just a tip of a cylindrical tube, in order to prevent damaging or otherwise misshaping the implantable medical device. Furthermore, the shaped tip can be shaped to facilitate reentry of devices deployed therefrom, such as deployment balloons. The enlarged and shaped tips allow for the shaft of the guide catheter to remain small to maintain flexibility. As such, the present disclosure describes systems of implantable medical devices and implantation instruments that can specifically function together to improve the outcome of the procedure, e.g., implanting the medical device in a precise location with a precise shape, in less time and with less difficulty.

The present inventors have recognized, among other things, that problems to be solved with guide catheters include the difficulty in balancing the ability to insert and flex the guide catheter while positioning within the anatomy and the ability of the guide catheter to receive other instruments. For example, thin or small diameter guide catheters, such as 8 French (~2.67 mm), can be easily flexed, but cannot receive large insertion instruments. Furthermore, smaller guide catheters can lead to difficulty in retrieving insertion instruments back into the guide catheter. For example, a balloon of an insertion instrument can sometimes not fully collapse to the pre-inflated size, thereby making retrieval of the balloon back into the guide catheter difficult. Furthermore, when attempting to retrieve devices into the guide catheter, the guide catheter can get pushed forward and lodged within the deployed device due to jostling of the guide catheter and the like.

The present subject matter can provide solutions to this problem and other problems, such as by providing a guide catheter having an enlarged tip. In various examples, the enlarged tip can guide, e.g., funnel, insertion instruments back into the guide catheter and prevent the guide catheter from undesirably engaging the deployed device. Additionally, in various examples, the enlarged tip can prevent the guide catheter from being pushed inside of the device being deployed or implanted. The enlarged tip can be located only at the distal end of the elongate guide catheter such that the main shaft of the guide catheter can be small and flexible, such as for vascular use.

The present inventors have recognized, among other things, that problems to be solved with guide catheters include the difficulty in determining the orientation of pre-curved guide catheters once inserted into the anatomy. For example, pre-curved guide catheters are intended to be placed within circuitous anatomy in a particular orientation such that the curvature of the guide catheter matches the path of the anatomy. However, the pre-curvature of the guide catheter can become distorted while be inserted through the anatomy, particularly as the guide catheter is rotated and jostled during the insertion process. As such, the guide catheter can become twisted, and the pre-curve can become misaligned with the anatomy. Thus, the guide catheter can become stressed and have undesirable curvatures introduced therein. Furthermore, the surgeon may not know which way the pre-curve of the guide catheter is facing, which can hinder delivery of a device with an insertion instrument catheter inserted into the guide catheter.

The present subject matter can provide solutions to this problem and other problems, such as by providing indicia on a proximal end portion if the guide catheter. The indicia can indicate a direction to which the distal portion of the guide catheter is curved. Furthermore, the indicia can indicate a plane in which the distal portion is curved to inform a surgeon about which direction the distal portion is biased. The surgeon can use the indicia to orient the guide catheter so that the pre-curve better aligns with the anatomy and thereby be better prepared to deliver a device using a guide catheter.

In an example, a guide catheter for cannulating a coronary sinus from a superior vena cava can comprise a flexible elongate shaft comprising a proximal portion, a pre-formed distal portion comprising a proximal straight zone, a proximal curved zone extending along a first curved path from the proximal straight zone, a distal straight zone extending along a straight path from the proximal curved zone and a distal curved zone extending along a second curved path from the distal straight zone, and a distal tip extending from the distal curved zone.

In another example, a guide catheter for delivering an expandable flow modifying apparatus to a heart passage can comprise a flexible elongate shaft comprising a proximal portion comprising a fitting for receiving an insertion instrument and distal portion comprising a distal tip, wherein the distal tip comprises an enlarged tip to prevent the flexible elongate shaft from passing through the expandable flow modifying apparatus.

In an additional example, a system for implanting a flow modifying device in vasculature of a heart can comprise a flow modifying device and a guide catheter. The flow modifying device can comprise a tubular body comprising a first opening located at a first end of the tubular body, a second opening located at a second end of the tubular body and a neck positioned between the first opening and the second opening. The guide catheter can comprise a flexible elongate shaft comprising a proximal portion comprising a fitting for receiving an insertion instrument and distal portion comprising a distal tip, wherein the distal tip comprises an enlarged tip to prevent the flexible elongate shaft from passing through the flow modifying device.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 1B is a side view of the guide catheter of FIG. 1A in a predisposed curved state.

FIG. 2 is a close-up, side view of a distal end portion of the guide catheter of FIG. 1B showing a plurality of curvature zones having pre-curvature.

FIG. 3 is a schematic illustration of a section of the guide catheter of FIGS. 1A and 1B showing various layers forming the guide catheter.

FIG. 5A is a schematic illustration showing a guide catheter having an insertion instrument inserted therein to expand a flow modifying device with a balloon.

FIG. 5B is a schematic illustration showing the guide catheter of FIG. 5A extended into the flow modifying device and the insertion instrument withdrawn therefrom.

FIG. 6B is a side view of the fitting of FIG. 6A showing a pair of wings extending from the coupler.

FIG. 7C is a perspective view of the distal end of the guide catheter of FIG. 7A projecting from a containment sheath.

FIG. 7D is a side view of the flared tip of the guide catheter of FIGS. 7A-7C engaged with a flow modifying device.

FIG. 8A is a perspective view of a distal end of a guide catheter of the present disclosure comprising a prolapse tip.

FIG. 8B is a side view of the distal end of FIG. 8A showing the prolapse tip.

FIG. 8C is a side cross-sectional view of the guide catheter of FIG. 8B showing a curved-back shape of the prolapse tip.

FIG. 9A is a perspective view of a distal end of a guide catheter of the present disclosure comprising a balloon tip.

FIG. 9B is a side view of the distal end of FIG. 9A showing the balloon tip.

FIG. 9C is a side cross-sectional view of the guide catheter of FIG. 9B showing an inflatable bladder of the balloon tip.

FIG. 10 is a side view of a distal end of a guide catheter of the present disclosure comprising a funnel tip.

Figure 1A:
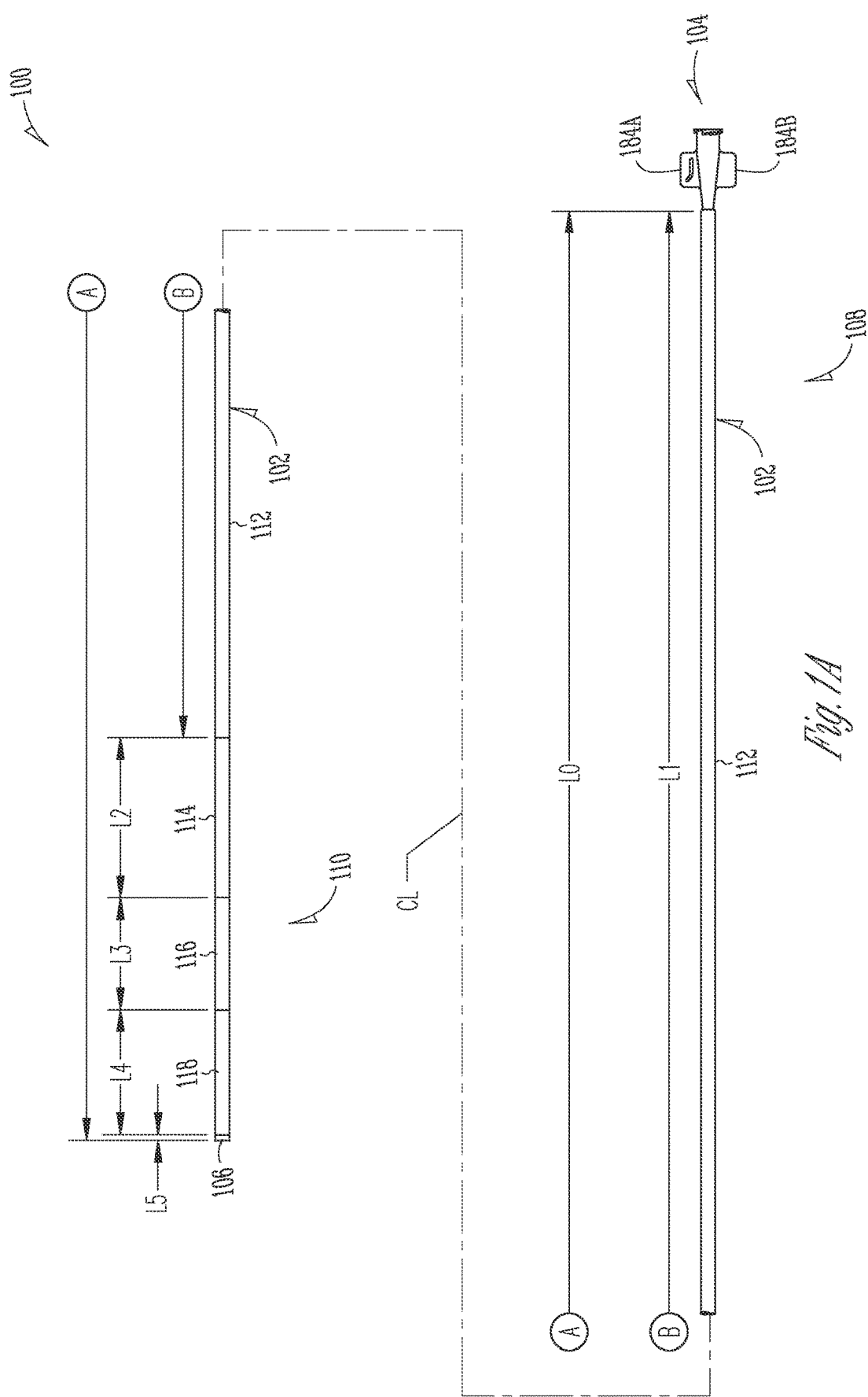
FIG. 1A is side view of a guide catheter of the present disclosure in an artificially straightened configuration to show different stiffness sections of a flexible elongate shaft.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1A is side view of guide catheter 100 of the present disclosure in an artificially straightened configuration to show different stiffness sections of a flexible elongate shaft. FIG. 1B is a side view of guide catheter 100 of FIG. 1A in a predisposed curved state showing a plurality of curvature zones having pre-curvature. As such, FIG. 1B shows guide catheter 100 at rest with no forces applied thereto and FIG. 1A shows theoretical straightening forces applied to guide catheter 100 to overcome the pre-curvature. Guide catheter 100 can comprise flexible elongate shaft 102, fitting 104 and tip 106. Flexible elongate shaft 102 can comprise a generally proximal portion 108 to which fitting 104 is attached and a generally distal portion 110 terminating at tip 106. FIGS. 1A and 1B are discussed concurrently unless otherwise specified.

With reference to FIG. 1A, guide catheter 100 can be straightened out along central longitudinal axis CL in order to view various lengths, e.g., the stiffness sections, of flexible elongate shaft 102. Flexible elongate shaft 102 can include an internal lumen, e.g., lumen 156 of FIG. 3, that extends along central longitudinal axis CL from a proximal end of fitting 104 through to the distal end of tip 106. Length L0 of flexible elongate shaft 102 can be divided into a plurality of stiffness sections between fitting 104 and tip 106. First stiffness section 112 can extend distally from fitting 104 to second stiffness section 114. Second stiffness section 114 can extend distally from first stiffness section 112 to third stiffness section. Third stiffness section 116 can extend distally from second stiffness section 114 to fourth stiffness section. Fourth stiffness section 118 can extend distally from third stiffness section 116 to tip 106. Tip 106 can be positioned at the distal end of fourth stiffness section 118 and can comprise a fifth stiffness section.

Stiffness sections 112-118 and tip 106 can be configured to have different stiffness properties or hardness properties in order to facilitate the insertion process, cooperation with another instrument inserted therein, such as an insertion instrument for a flow modifying device, and the withdrawal process. In examples, sections 112-118 can become progressively less stiff or more flexible from proximal portion 108 to distal portion 110.

In examples, length L0 of flexible elongate shaft 102 can be approximately 610 millimeters+/−10 millimeters. First stiffness section 112 can have length L1. In examples, length L1 can be approximately 485 millimeters. Second stiffness section 114 can have length L2. In examples, length L2 can be approximately 50 millimeters. Third stiffness section 116 can have length L3. In examples, length L3 can be approximately 35 millimeters. Fourth stiffness section 118 can have length L4. In examples, length L4 can be approximately 38 millimeters. Tip 106 can have length L5. In examples, length L5 can be approximately 2 millimeters+/−0.5 millimeters.

In examples, diameter D1 can be approximately 0.122 inches, or in the range of approximately 0.118 millimeters inches to approximately 0.123 inches. In additional examples, diameter D1 can be approximately 8 French, 9 French or 10 French and sizes in between.

In examples, the internal lumen within flexible elongate shaft 102, i.e., lumen 156 of FIG. 3, can have a diameter of approximately 0.102 millimeters, or in the range of approximately 0.099 millimeters to approximately 0.103 millimeters.

In examples, first stiffness section 112 can be comprised of a flexible material that is sufficiently stiff to facilitate insertion through long lengths of anatomy and that can resist bending from an insertion instrument inserted therein. In examples, first stiffness section 112 can be stiffer than stiffness sections 114-118 and tip 106. In examples, first stiffness section 112 can have a hardness of 72 on the Shore D scale. In examples, first stiffness section 112 can have a hardness in the range of approximately 67 Shore D to approximately 77 Shore D. In examples, first stiffness section 112 can be made of a polymer, such as Polyether block amide (PEBA). In examples, first stiffness section 112 can be made of Pebax® material, such as Pebax 7233D, commercially available from Arkema.

In examples, second stiffness section 114 can be comprised of material that is less stiff than the material of stiffness section 112. In examples, second stiffness section 114 can have a hardness of 63 on the Shore D scale. In examples, second stiffness section 114 can have a hardness in the range of approximately 58 Shore D to approximately 68 Shore D. In examples, second stiffness section 114 can be made of a polymer, such as Polyether block amide (PEBA). In examples, second stiffness section 114 can be made of Pebax® material, such as Pebax 6333, commercially available from Arkema.

In examples, third stiffness section 116 can be comprised of material that is less stiff than the material of stiffness section 114. In examples, third stiffness section 116 can have a hardness of 55 on the Shore D scale. In examples, third stiffness section 116 can have a hardness in the range of approximately 50 Shore D to approximately 65 Shore D. In examples, third stiffness section 116 can be made of a polymer, such as Polyether block amide (PEBA). In examples, third stiffness section 116 can be made of Pebax® material, such as Pebax 5533, commercially available from Arkema.

In examples, fourth stiffness section 118 can be comprised of material that is less stiff than the material of stiffness section 116. In examples, fourth stiffness section 118 can have a hardness of 35 on the Shore D scale. In examples, fourth stiffness section 118 can have a hardness in the range of approximately 30 Shore D to approximately 40 Shore D. In examples, fourth stiffness section 118 can be made of a polymer, such as Polyether block amide (PEBA). In examples, fourth stiffness section 118 can be made of Pebax® material, such as Pebax 4033, commercially available from Arkema.

In examples, tip 106, which can comprise a fifth stiffness section, can be comprised of material that is less stiff than the material of stiffness section 118. In examples, tip 106 can have a hardness of 25 on the Shore D scale. In examples, tip 106 can have a hardness in the range of approximately 20 Shore D to approximately 40 Shore D. In examples, tip 106 can be made of a polymer, such as Polyether block amide (PEBA). In examples, tip 106 can be made of Pebax® material, such as Pebax 2533, commercially available from Arkema.

The stiffness or hardness properties of stiffness sections 112-118 can additionally be identified on guide catheter 100. In examples, textual or numerical indicia can be printed on stiffness sections 112-118 to provide the stiffness of each section. In examples, stiffness sections 112-118 can be color coded, such as by having section 112 being the darkest colored section and sections 114-118 becoming progressively lighter in color. In examples, first stiffness section 112 can have a color additive of 20% BaSO4 to produce a color of Pantone 3265C, second stiffness section 114 can have a color additive of 20% BaSO4 to produce a color of Pantone 3258C, third stiffness section 116 can have a color additive of 20% BaSO4 to produce a color of Pantone 571C, fourth stiffness section 118 can have a color additive of 20% BaSO4 to produce a color of Pantone 573C. and tip 106 can have a color additive of 20% BaSO4 to produce a color of Pantone 573C.

Furthermore, the material of stiffness sections 112-118 and tip 106 can include an additive to facilitate radiopacity, such as barium sulfate, bismuth or tungsten. In particular, tip 106 can have radiopaque properties to facilitate insertion of usage of guide catheter 100.

The differing stiffnesses of stiffness section 112-118 and tip 106 can facilitate insertion and usage of guide catheter 100. For example, the increased stiffnesses toward proximal portion 108 can facilitate advancement through anatomy, such as by pushing, during insertions. Additionally, the increased stiffnesses toward proximal portion 108 can inhibit deflection of guide catheter 100 during insertion of other instruments through guide catheter 100. Meanwhile, the increased flexibility toward distal portion 110 can facilitate flexing of guide catheter 100 to allow for precise placement and can prevent damage to tissue.

With reference to FIG. 1B, distal portion 110 can be pre-curved so flexible elongate shaft 102 is curved back toward fitting 104 and tip 106 points radially outwardly with a slight proximal orientation. Flexible elongate shaft 102 can have proximal straight zone 120, proximal curved zone 121, distal straight zone 124 and distal curved zone 126.

In examples, guide catheter 100 can have at least two curvature zones and one straight zone. In examples, guide catheter 100 can have two curvature zones separated by a straight zone. In examples, each of the curved zones can have sections with different radii of curvature.

As discussed with reference to FIG. 2, zones 120-126 can facilitate conformance of guide catheter 100 to particular anatomic features, which can facilitate insertion of guide catheter 100 and insertion of other instrument through guide catheter 100.

FIG. 2 is a close-up side view of distal portion 110 of guide catheter 100 of FIG. 1B showing a plurality of curvature zones having pre-curvature. Proximal straight zone 120 and distal straight zone 124 can have curvatures of zero. Proximal curved zone 121 can have first segment 122 and second segment 123. Distal curved zone 126 can have first segment 128, second segment 130, third segment 132, fourth segment 134 and fifth segment 136.

Zones 120-126 can be correlated to stiffness section 112-118 and tip 106. Proximal straight zone 120 and proximal curved zone 121 can comprise first stiffness section 112. Distal straight zone 124 and first segment 128 can comprise second stiffness section 114. Second segment 130 and third segment 132 can comprise third stiffness section 116. Fourth segment 134 and fifth segment 136 can comprise fourth stiffness section 118.

Proximal straight zone 120 can extend from fitting 104 to proximal curved zone 121. Proximal curved zone 121 can extend from proximal straight zone 120 to distal straight zone 124. First segment 122 can extend from proximal straight zone 120 to second segment 123. Second segment 123 can extend from first segment 122 to distal straight zone 124. Distal straight zone 124 can extend from proximal curved zone 121 to first segment 128. First segment 128 can extend from distal straight zone 124 to second segment 130. Second segment 130 can extend from first segment 128 to third segment 132. Third segment 132 can extend from second segment 130 to fourth segment 134. Fourth segment 134 can extend from third segment 132 to fifth segment 136. Fifth segment 136 can extend from fourth segment 134 to tip 106.

Proximal straight zone 120 can have a length less than length L1, which is the length of first stiffness section 112 (FIG. 1A). In examples, proximal straight zone 120 can have a linear length of approximately 412 millimeters+/−10 millimeters.

First segment 122 of proximal curved zone 121 can have radius of curvature R1. In examples, radius of curvature R1 can be approximately 794.37 millimeters. In examples radius of curvature R1 can be in the range of approximately 784 millimeters to approximately 804 millimeters. In examples, first segment 122 can have an arc length of approximately 45 millimeters+/−5 millimeters.

Second segment 123 of proximal curved zone 121 can have radius of curvature R2. In examples, radius of curvature R2 can be approximately 219.15 millimeters. In examples radius of curvature R2 can be in the range of approximately 209 millimeters to approximately 229 millimeters. In examples, second segment 123 can have an arc length of approximately 28 millimeters+/−5 millimeters.

Distal straight zone 124 can have length L7. In examples, distal straight zone 124 can have a linear length of approximately 32.5 millimeters+/−5 millimeters.

First segment 128 of distal curved zone 126 can have radius of curvature R3. In examples, radius of curvature R3 can be approximately 71.7 millimeters. In examples, radius of curvature R3 can be in the range of approximately 61 millimeters to approximately 81 millimeters. In examples, first segment 128 can have an arc length of approximately 17.5 millimeters+/−5 millimeters.

Second segment 130 of distal curved zone 126 can have radius of curvature R4. In examples, radius of curvature R4 can be approximately 26.18 millimeters. In examples, radius of curvature R4 can be in the range of approximately 21 millimeters to approximately 31 millimeters. In examples, second segment 130 can have an arc length of approximately 14 millimeters+/−5 millimeters.

Third segment 132 of distal curved zone 126 can have radius of curvature R5. In examples, radius of curvature R5 can be approximately 35.63 millimeters. In examples, radius of curvature R5 can be in the range of approximately 30 millimeters to approximately 40 millimeters. In examples, third segment 132 can have an arc length of approximately 21 millimeters+/−5 millimeters.

Fourth segment 134 of distal curved zone 126 can have radius of curvature R6. In examples, radius of curvature R6 can be approximately 68.19 millimeters. In examples, radius of curvature R6 can be in the range of approximately 63 millimeters to approximately 73 millimeters. In examples, fourth segment 134 can have an arc length of approximately 16 millimeters+/−5 millimeters.

Fifth segment 136 of distal curved zone 126 can have radius of curvature R7. In examples, radius of curvature R7 can be approximately 125.75 millimeters. In examples radius of curvature R7 can be in the range of approximately 115 millimeters to approximately 135 millimeters. In examples, fifth segment 136 can have an arc length of approximately 22 millimeters+/−5 millimeters.

As mentioned, tip 106 can have a linear length of approximately 2.0 millimeters+/−0.5 millimeters.

Radius of curvatures R1 and R2 of proximal curved zone 121 can result in the distal end of first stiffness section 112 being disposed at angle A1 relative to proximal straight zone 120. In examples, angle A1 can be approximately 10.5 degrees. In examples, angle A1 can be in the range of approximately 8.5 degrees to approximately 12.5 degrees.

Radius of curvature R3 of first segment 128 can result in the distal end of second stiffness section 114 being disposed at angle A2 relative to proximal straight zone 120. In examples, angle A2 can be approximately 28.2 degrees. In examples, angle A2 can be in the range of approximately 23 degrees to approximately 33 degrees.

Radius of curvature R4 of second segment 130 and radius of curvature R5 of third segment 132 can result in the distal end of third stiffness section 116 being disposed at angle A3 relative to proximal straight zone 120. In examples, angle A3 can be approximately 86.5 degrees. In examples, angle A3 can be in the range of approximately 76 degrees to approximately 96 degrees.

Radius of curvature R6 of fourth segment 134 and radius of curvature R7 of fifth segment 136 can result in the distal end of fourth stiffness section 118 being disposed at angle A4 relative to proximal straight zone 120. In examples, angle A4 can be approximately 62.0 degrees. In examples, angle A4 can be in the range of approximately 52 degrees to approximately 72 degrees.

As discussed in greater detail with reference to FIGS. 4A and 4B, zones 120-126 can be configured to extend along a natural anatomic path. In the disclosed example, zones 120-126 mimic the path produced by a superior vena cava, a right atrium and a coronary sinus. In other examples, guide catheter 100 can be shaped to conform to other anatomic pathways, such as other vasculature pathways.

FIG. 3 is a schematic illustration of a portion of guide catheter 100 of FIGS. 1A and 1B showing various layers forming flexible elongate shaft 102. Flexible elongate shaft 102 can comprise inner layer 150, reinforcement layer 152 and outer layer 154. Lumen 156 can extend through flexible elongate shaft 102. In an example, inner layer 150, reinforcement layer 152 and outer layer 154 can comprise a single integrated unit wherein outer layer 154, reinforcement layer 152 and inner layer 150 are pre-assembled into unit defining lumen 156 extending along centerline CL. In examples, inner layer 150 and outer layer 154 can be formed around, e.g., melted around, reinforcement layer 152.

Outer layer 154 can comprise a protective cover for other components of guide catheter 100. Outer layer 154 can comprise a waterproof, biocompatible material defining a lumen for the location of other components, such as reinforcement layer 152 and inner layer 150. Materials used to form outer layer 154 can vary depending upon the stiffness desired for guide catheter 100. In examples, outer layer 154 can be fabricated from polyamides, such as Nylon and DURETHAN®, commercially available from Bayer, polyetheretherketone (PEEK), polyimide (PI), and polyetherimide (PEI). As discussed, outer layer 154 can be fabricated from polyether block amide (PEBA). In examples, outer layer 154 can be fabricated from a polyamide such as CRISTAMID®, commercially available from Arkema, which imparts a slightly less rigid durometer than the rigid polyamides and slightly greater than the flexible PEBA material. In examples, the material of outer layer 154 can have crystal growth rates that support a crystalline morphology. Moreover, these materials can have crystal growth rates that permit their crystalline microstructure to be modified during the nucleation process, thereby facilitating pre-forming of curvatures. In additional examples, outer layer 154 can be fabricated from materials having a rapid crystallization growth rate that do not provide a crystalline morphology conducive to pre-forming curvatures. In such examples, nucleating agents can be added to the material to facilitate formation of crystal structures.

Reinforcement layer 152 can comprise a tubular body formed of individual strands or bundles of strands woven, weaved or braided together to form a tube-like body. In examples, reinforcement layer 152 can comprise wire mesh tubing fabricated from metallic strands, such as stainless steel. In examples, reinforcement layer 152 can comprise a braided reinforcement with a 16 carrier construction in a herringbone pattern made from 0.002 inch (0.0508 mm) wire of 304 stainless steel and wound with a picks per inch of length (PPI) of 90. Reinforcement layer 152 can be used to provide reinforcement to outer layer 154, such to provide extra stiffening properties or prevent radial expansion. In other examples, reinforcement layer 152 can comprise a spiral band tubing formed of one or more strands of material wound spirally into a helix. Reinforcement layer 152 can extend along the entirety of flexible elongate shaft 102 or only portions of flexible elongate shaft 102. In examples, reinforcement layer 152 can extend from fitting 104 to before tip 106, at the distal end of fourth stiffness section 118 or short of the distal end of fourth stiffness section 118.

Inner layer 150 can define lumen 156, which provides a passage for another instrument or device through guide catheter 100. Lumen 156 of inner layer 150 can be lined with a coating or material to reduce friction therein and facilitate sliding of instruments therein. In examples lumen 156 can be lined with polytetrafluoroethylene (PTFE). In examples, inner layer 150 can be made of the same materials listed above for outer layer 154. In examples, inner layer 150 and outer layer 154 can be made of the same material. In other examples, inner layer 150 and outer layer 154 can be made of different materials.

In order to introduce pre-curvature into guide catheter 100, the material of flexible elongate shaft 102 can be positioned around a shape mandrel that can be shaped to the desired curvature and then heated to allow the material to take the shape of the mandrel by allowing the polymer crystals to form at a slow growth rate to retain the curvature of the mandrel. For example, guide catheter 100 can be heated at about 280° Fahrenheit (~138° Celsius). In examples, manufacturing of guide catheter 100 and the pre-curvatures imparted therein can be performed using conventional manufacturing techniques known in the art.

Figure 4A:
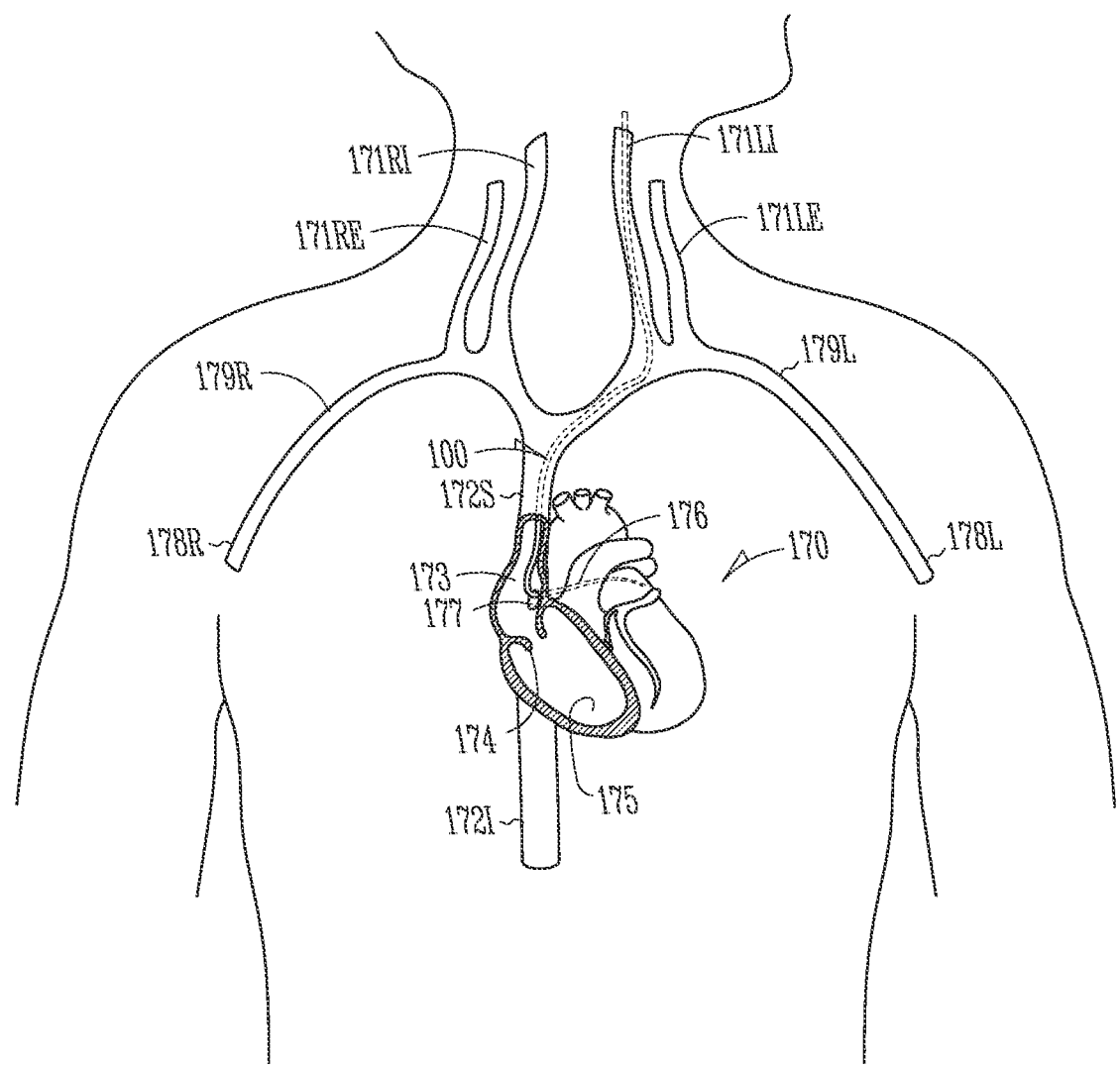
FIG. 4A is a schematic illustration of a human heart and associated vasculature with a guide catheter inserted therein.

FIG. 4A is a schematic illustration showing guide catheter 100 deployed in human heart 170. Heart 170 comprises Superior vena cava 172S, right atrium 173, tricuspid valve 174 and right ventricle 175. Right atrium 173 can be connected to coronary sinus 176 via coronary sinus ostium 177. During normal operation of the heart 170, deoxygenated blood is fed into right atrium 173 through superior vena cava 172S and inferior vena cava 172I. The major veins supplying blood to the superior vena cava 172S include the right and left axillary veins 178R and 178L, which flow into the right and left subclavian veins 179R and 179L. The right and left external jugular 171RE and 171LE, along with the right and left internal jugular 171RI and 171LI, join the right and left subclavian veins 179R and 179L to form the right and left brachiocephalic veins. The right and left brachiocephalic veins combine to flow into the superior vena cava 172S.

In examples, catheter 100 can be introduced into the coronary sinus 176 via jugular access. In specific examples, catheter 100 can be introduced through the right external jugular vein 171RE. In the illustrated example, guide catheter 100 can be inserted into jugular 171LI, superior vena cava 172S, right atrium 173, sinus ostium 177 and coronary sinus 176. As such tip 106 (FIG. 1A) can be located in coronary sinus 176 to, for example, deliver flow modifying device 202 (FIG. 4A). In other examples of the present invention, catheter 100 can enter the vascular system through the left axillary vein 178L, right external jugular 171RE, left internal jugular 171LI, or the left brachiocephalic vein.

In examples, coronary sinus 176 can be reached with guide catheter 100 via a subclavian route or via transfemoral route.

Figure 4B:
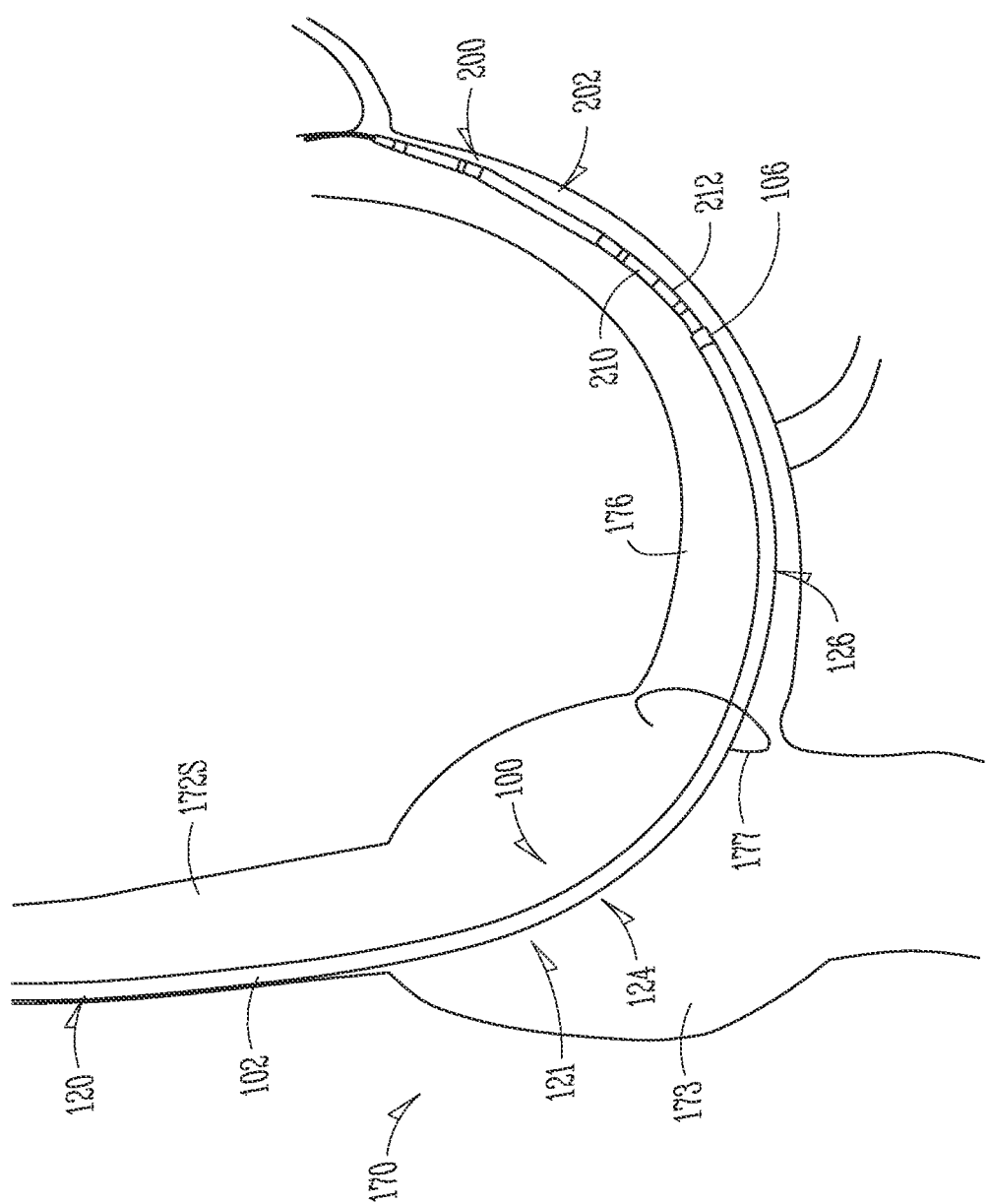
FIG. 4B is a schematic illustration of a guide catheter of the present disclosure inserted into a coronary sinus of a human heart.

FIG. 4B is a schematic illustration of guide catheter 100 of the present disclosure inserted into heart 170. Heart 170 can comprise superior vena cava 172S, right atrium 173, coronary sinus ostium 177 and coronary sinus 176.

Guide catheter 100 can be pre-shaped to match the anatomy of the desired insertion path. In examples guide catheter 100 can be pre-shaped to match the shape of superior vena cava 172S, coronary sinus ostium 177 and coronary sinus 176. In particular, proximal straight zone 120 can be shaped to extend along superior vena cava 172S, proximal curved zone 121 and distal straight zone 124 can be shaped to extend through right atrium 173, and distal curved zone 126 can be shaped to extend through coronary sinus 176. Distal straight zone 124 can be positioned by proximal curved zone 121 to extend across all or a portion of right atrium 173. The straightness of distal straight zone 124 can resist bending of guide catheter 100 away from coronary sinus ostium 177 as instrumentation is being deployed through guide catheter 100. Distal curved zone 126 can extend through coronary sinus ostium 177 and into coronary sinus 176. The curvatures of distal curved zone 126 can be facilitate entry into coronary sinus ostium 177 and extension along coronary sinus 176, thereby reducing stress on coronary sinus ostium 177 and coronary sinus 176 and reducing pushing of tissue against guide catheter 100.

As shown in FIG. 4B, guide catheter 100 can be inserted into heart 170 to locate tip 106 within coronary sinus 176. Thereafter, another instrument, such as an insertion device or catheter can be inserted into guide catheter 100 to deliver an implant or prosthetic device to coronary sinus 176. In the illustrated example, the insertion device can comprise balloon catheter 200 used to position flow modifying device 202. Flow modifying device 202 is illustrated in FIG. 4B in a non-deployed state collapsed to a small diameter suitable for passage through lumen 156 (FIG. 3) of guide catheter 100.

FIG. 5A is a schematic illustration showing guide catheter 100 having balloon catheter 200 inserted therein to expand flow modifying device 202. Flow modifying device 202 can comprise inflow portion 204, outflow portion 206 and restriction portion 208. Balloon catheter 200 can be used to insert balloon 210 into flow modifying device 202 and inflate balloon 210 to expand flow modifying device 202 to the illustrated deployed shape. Prior to deployment, flow modifying device 202 can be collapsed to approximately the diameter of shaft 212 of balloon catheter 200. Balloon catheter 200 can be configured to deploy inflow portion 204 distally of outflow portion 206. In other configurations, balloon catheter 200 can be configured to insert flow modifying device 202 in the opposite orientation such that inflow portion 204 faces toward balloon catheter 200. Guidewire 213 can be used to position shaft 212 of balloon catheter 200 within anatomy.

Flow modifying device 202 can be configured to reduce blood flow therethrough in one direction. In examples, inflow portion 204 can be smaller than outflow portion 206. In examples, one of inflow portion 204 and outflow portion 206 can be omitted. Inflow portion 204 and outflow portion 206 can comprise flared sections that are reduced in diameter leading into restriction portion 208. Thus, wall of inflow portion 204 and outflow portion 206 can be inclined relative to the wall of coronary sinus 176 (FIG. 4A) and walls of restriction portion 208 can be parallel or nearly parallel to the wall of coronary sinus 176.

Flow modifying device 202 can be radially expandable, which can cause a corresponding reduction in length of flow modifying device 202. In examples, flow modifying device 202 can have a length of approximately 20 mm before expansion and about 18.8 mm after expansion. An exemplary thickness of the material of flow modifying device 202 can be approximately 0.15 mm, however, thinner or thicker materials can be used. Other exemplary lengths of flow modifying device 202 are 5 mm, 12 mm, 24 mm, 35 mm 45 mm and any smaller, intermediate or larger size. The length is optionally selected to match a physiological size of the target vein (e.g., length and curves) and/or to ensure good contact with vein walls. The length of restriction portion 208 can be, for example, 0.5 mm, 1 mm, 2 min, 3 mm, 5 mm or any smaller, intermediate or larger length, for example selected to achieve desired flow dynamics. An exemplary inner diameter of inflow portion 204 and outflow portion 206 can be between 2 mm and 30 mm, for example, 5 mm, 10 mm, 15 mm, 20 mm or any larger, smaller or intermediate diameter, for example selected to match the vein diameter. The inner diameter of restriction portion 208 can be, for example, 1 mm, 2 mm, 3 mm, 5 mm, 10 mm or any smaller, larger or intermediate diameter, for example selected to achieve desired flow dynamics and/or a pressure differential across the flow modifying device.

In an exemplary embodiment of the invention, the ratio between the cross-section of restriction portion 208 and inflow portion 204 and outflow portion 206 can be 0.9, 0.8, 0.6, 0.4, 0.2 or any larger, smaller or intermediate ratio, for example selected to achieve desired flow dynamics and/or a pressure differential across flow modifying device 202.

While a circular cross-section is shown, other cross-sections may be used, for example, polygona and ellipsoid. A potential advantage of non-circular cross-sections is that the implant is less likely to migrate axially and/or rotate. Alternatively or additionally, the outside of flow modifying device 202 can be roughened and/or otherwise adapted to adhere to the vein wall. The cross-section shape and/or orientation can optionally change along the length of flow modifying device 202.

In examples, flow modifying device 202 can be fabricated from a mesh-type material, such as a woven open material of metal and/or plastic fibers, using methods well known in the art. In examples, flow modifying device 202 can be formed by cutting a sheet of metal or a tube, for example, using laser, water cutting, chemical erosion or metal stamping (e.g., with the result being welded to form a tube). In examples, all or portions of flow modifying device 202 can be covered via a cover of fabric, plastic, tissue or the like.

In examples, flow modifying device 202 can be constructed similarly to the devices described in US 2020/0178978 A1 to Shmuel et al. titled "Methods for treating abnormal growth in the body using a flow reducing implant," the contents of which are hereby incorporated herein by this reference.

In the deployed state, flow modifying device 202 can comprise diameter D2 at restriction portion 208 and diameter D3 at outflow portion 206. In examples, inflow portion 204 and outflow portion 206 can have the same diameter. In examples, inflow portion 204 can be larger than outflow portion 206.

Fluid, such as an 80/20 blend of saline and contrast media, can be introduced into balloon 210 via shaft 212 to expand flow modifying device 202. Either before, during or after expansion, a surgeon can position flow modifying device 202 into the desired position. Once properly positioned and expanded to the desired diameter, balloon catheter 200 can be separated from flow modifying device 202 to leave flow modifying device 202 deployed and implanted in the anatomy. In order to retract balloon catheter 200 back into guide catheter 100, balloon catheter 200 can be retracted proximally into guide catheter 100 to bring balloon 210 inside of guide catheter 100. However, balloon 210 does not always fully deflate when application of compressed air is stopped due to, for example, stretching of the material of balloon 210. As such when balloon catheter 200 is pulled proximally, material of balloon 210 can engage tip 106 and outer surfaces of guide catheter 100. In some cases, the engagement of the material of balloon 210 with guide catheter 100 can cause tip 106 of guide catheter 100 to invaginate or close in on itself, thereby making advancement of balloon 210 into guide catheter 100 difficult or impossible. As such, guide catheter 100 can comprise enlarged tip 214, as shown in FIG. 5B, to facilitate insertion of balloon 210 into guide catheter 100. In examples, enlarged tip 214 can be shaped to gently engage balloon 210 to urge balloon 210 in a deflated state back into guide catheter 100.

FIG. 5B is a schematic illustration showing guide catheter 100 of FIG. 5A extended into flow modifying device 202. In the example of FIG. 5B, guide catheter 100 includes enlarged tip 214. As balloon 210 is being advanced into guide catheter 100, it can become possible for guide catheter 100 to advance forward or distally to engage flow modifying device 202. In some cases, the distal tip of guide catheter 100 can become lodged inside of restriction portion 208. For example, diameter D3 of deployed flow modifying device 202 and the outer diameter D1 of guide catheter 100 can both be 9 French, thereby making it possible for tip 106 (FIG. 1A) of guide catheter 100 to become pushed into restriction portion 208. As such, guide catheter 100 can comprise enlarged tip 214 to prevent engagement of guide catheter 100 with restriction portion 208. Various configurations of enlarged tips suitable for use as enlarged tip 214 are described with reference to FIGS. 7A-10.

Figure 6A:
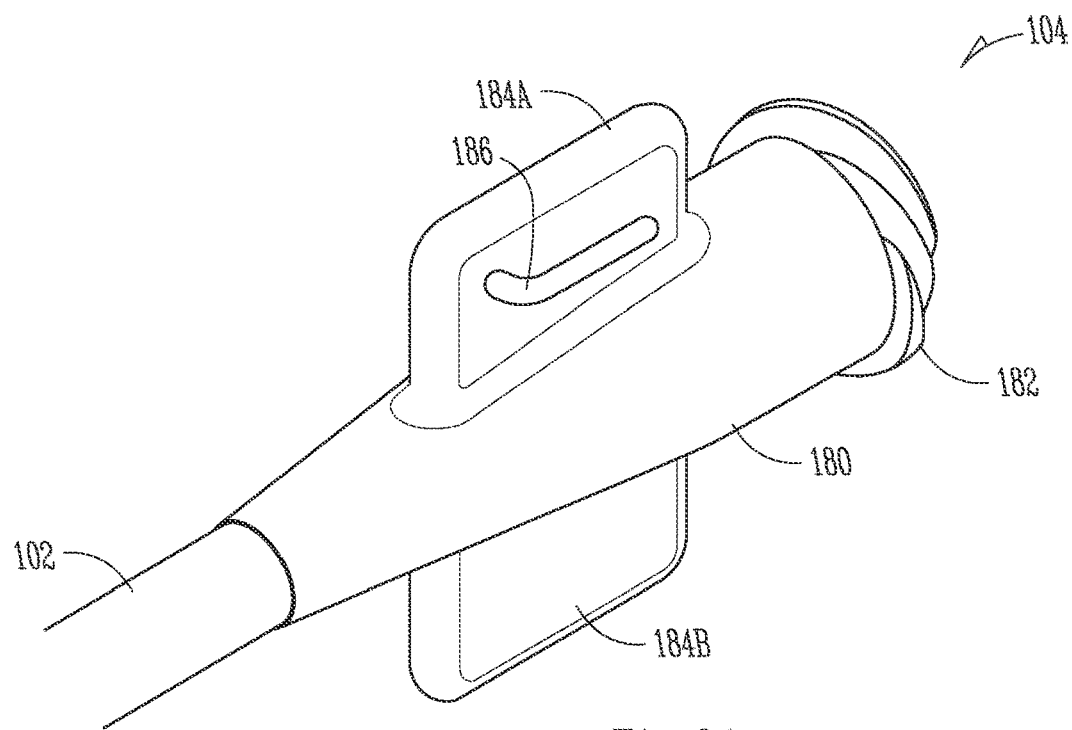
FIG. 6A is a perspective view of a proximal end of a guide catheter of the present disclosure comprising a fitting having pre-curvature indicia located thereon.
Figure 6C:
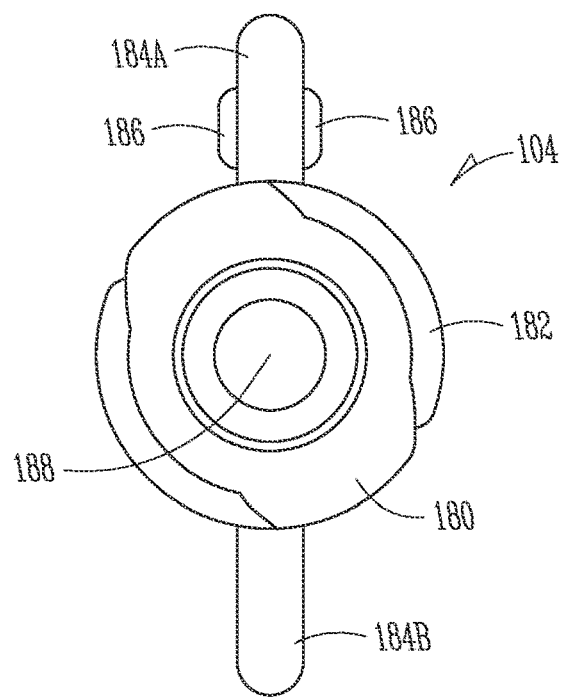
FIG. 6C is an end view of the fitting of FIG. 6A showing indicia located opposite sides of one of the wings.

FIG. 6A is a perspective view of proximal portion 108 of guide catheter 100 of the present disclosure comprising fitting 104. FIG. 6B is a side view of fitting 104 of FIG. 6A comprising annular body 180 and coupler 182. FIG. 6C is an end view of fitting 104 of FIG. 5A showing wings 184A and 184B extending from coupler 182. Wing 184A can include indicia 186. FIGS. 6A-6C are discussed concurrently.

Fitting 104 can comprise a device that facilitates coupling of flexible elongate shaft 102 to another device, such as an insertion instrument for an implantable medical device. Fitting 104 can comprise annular body 180 comprising coupler 182 and can be located at a proximal end of annular body 180 to allow another device to attach to fitting 104. Coupler 182 can comprise a flange. In examples, the flange of coupler 182 can include elements to allow other device to engage with coupler 182, such as one or more threads, notches, grooves and the like. In the illustrated example, coupler 182 can include helical slots for a twist-lock mechanism. In examples, fitting 104 can comprise a female Luer adapter.

In examples, guide catheters can be used to guide deployable prosthetic devices through guide catheter 100. Annular body 180 can comprise passageway 188 that can connect to lumen 156 (FIG. 3) within flexible elongate shaft 102. As such, passageway 188 can continuously extend from the proximal end of annular body 180 to tip 106 (FIG. 1A). Passageway 188 can be flared such that the proximal end is larger than the distal end to facilitate insertion of other devices into fitting 104 and subsequently into lumen 156.

Indicia 186 can be located on wing 184A. Indicia 186 can comprise visual or tactile feedback to a user regarding the orientation of tip 106 relative to fitting 104. In particular, indicia 186 can indicate the direction to which tip 106 is predisposed to curve. In the illustrated example, indicia 186 comprises elongate body 190 having proximal end 192A, distal end 192B and curved portion 194. In examples, indicia 186 can be located on both sides of wing 184A. Thus, elongate body 190 can extend through from one face of wing 184A to the opposing face of wing 184A such that elongate body 190 has the same shape throughout.

Elongate body 190 can extend parallel to the proximal portion of flexible elongate shaft 102 from proximal end 192A to curved portion 194, and curved portion 194 can extend radially away from the proximal portion of flexible elongate shaft 102 so that distal end 192B is positioned radially outward of proximal end 192A relative to the axis of flexible elongate shaft 102. Distal end 192B can, therefore, project in the same direction that tip 106 of guide catheter projects. Stated another way, the plane in which proximal end 192A and distal end 192B curve can be the same plane in which flexible elongate shaft 102 is pre-curved, e.g., tip 106 curves away from the proximal portion of flexible elongate shaft 102 in the same planar direction that distal end 192B curved away from proximal end 192A.

Elongate body 190 can comprise a raised protrusion that projects outward from wing 184A. As such, elongate body 190 can provide tactile feedback to a user. For example, a user can slide a fingertip or thumb over indicia 186 while looking elsewhere to gain an understanding of the direction of the pre-curvature of guide catheter 100. In other examples, indicia 186 can comprise other shapes or geometries. For example, elongate body 190 can be recessed or engraved into wing 184A. In examples, indicia 186 can comprise an arrow pointing in the direction of pre-curvature. In examples, textual indicia can be used, such as a statement comprising "Pre-curved in this direction" or words to that effect.

Figure 7A:
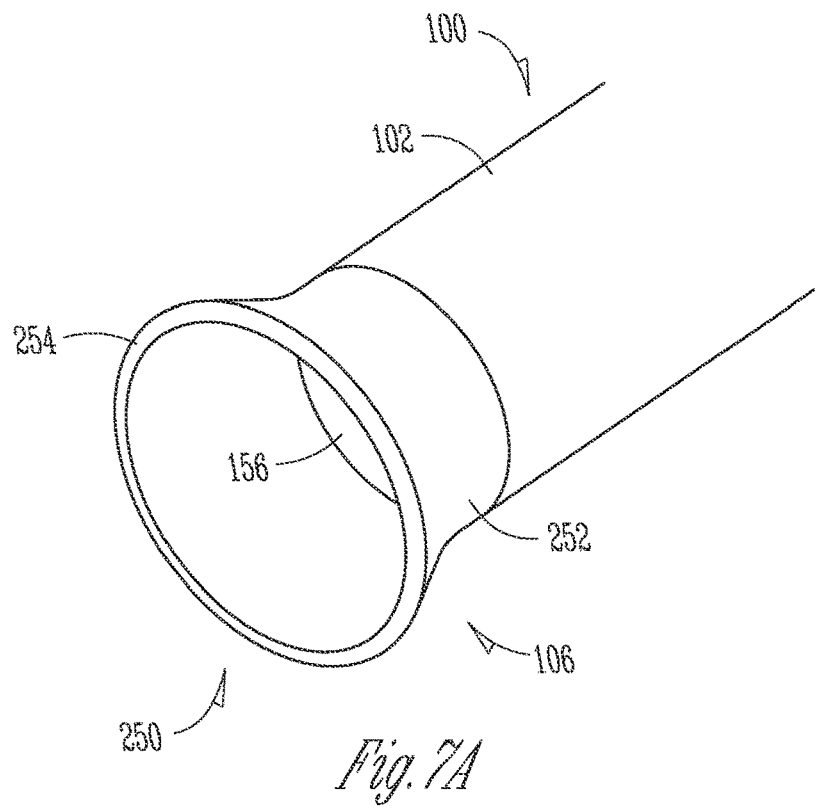
FIG. 7A is a perspective view of a distal end of a guide catheter of the present disclosure comprising a flared tip.
Figure 7B:
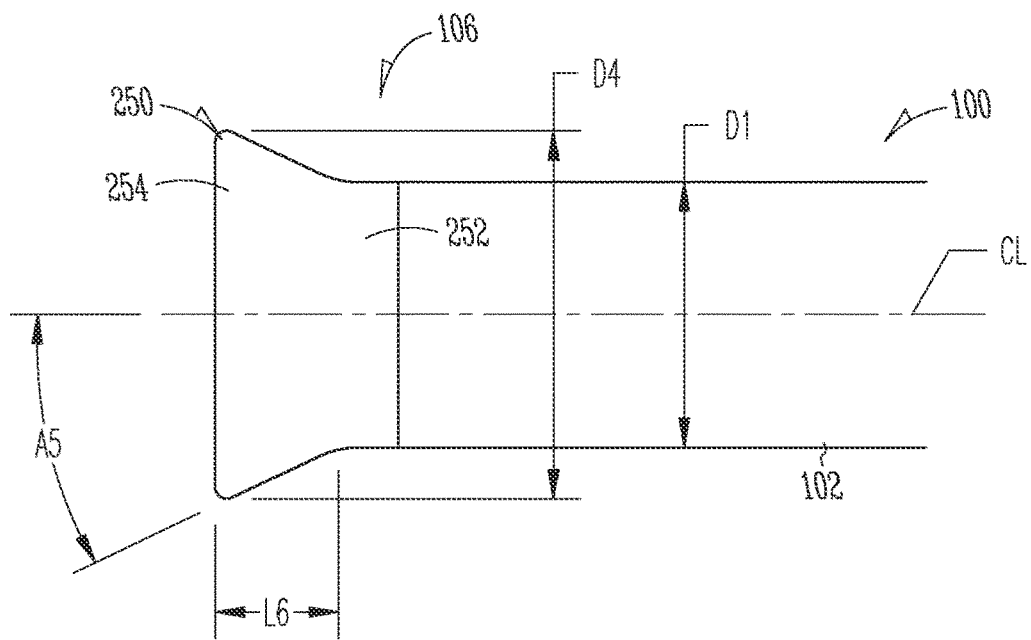
FIG. 7B is a side view of the distal end of FIG. 7A showing the flared tip.

FIG. 7A is a perspective view of distal portion 110 of guide catheter 100 of the present disclosure comprising flared tip 250. FIG. 7B is a side view of distal portion 110 of FIG. 7A showing flared tip 250. FIGS. 7A and 7B are discussed concurrently.

Flared tip 250 can comprise an extension of tip 106 of FIGS. 1A-2. Flared tip 250 can comprise annular rim 252 and conical rim 254. Flared tip 250 can extend from flexible elongate shaft 102 relative to central longitudinal axis CL at angle A5.

Flared tip 250 can comprise an extension of the material of flexible elongate shaft 102. In particular, conical rim 254 can comprise tip 106 (FIG. 1A) and conical rim 254 can comprise an extension of tip 106. In other examples, flared tip 250 can comprise an attachment to flexible elongate shaft 102.

Diameter D1 of flexible elongate shaft 102 can be selected to fit within a desired anatomy, such as a coronary sinus. In examples, diameter D1 can be in the range of approximately 8 French (2.667 mm) to approximately 10 French (3.33 mm). In a specific example, diameter D1 can be approximately 9 French (3 mm).

Angle A5 can be selected to provide a widened end for flexible elongate shaft 102 to more readily allow other components to be pulled proximally into flexible elongate shaft 102. Thus, conical rim 254 can have the same or approximately the same thickness as other portions of flexible elongate shaft 102. However, the opening within conical rim 254 can be wider than lumen 156 (FIG. 3) within flexible elongate shaft 102. Angle A5 can be selected such that diameter D4 is larger than diameter D1. In examples, angle A5 can be in the range of approximately fifteen degrees to approximately forty-five degrees. In a specific example, angle A5 can be approximately thirty degrees. In example, the axial length L6 of conical rim 254, e.g., the distance covered relative to central longitudinal axis CL, can be approximately 0.5 mm to approximately 2.5 mm. Angle A5 and length L6 can be varied to achieve the desired value of diameter D4. Diameter D4 can be approximately 0.25 mm to 0.5 mm larger than diameter D2 of restriction portion 208 of flow modifying device 202, which can allow for guide catheter 100 to be used to hold restriction portion 208 of flow modifying device 202 in place while withdrawing balloon 210, as shown in FIG. 7D. Diameter D4 can be selected to be approximately 0.25 mm to approximately 0.5 mm larger than diameter D1. In a particular example, D2 can be approximately 10 French.

Thus, as discussed with reference to FIG. 5B, conical rim 254 can be sized and shaped to provide at least two functions. First, conical rim 254 can allow balloon 210 (FIG. 5A) to be guided back into flexible elongate shaft 102. Angle A5 can be selected to generally conform to the shape of balloon 210. For example, angle A5 can be selected to be tangent to curved surfaces of balloon 210 facing toward flared tip 250, thereby facilitating funneling material of balloon 210 back into guide catheter 100. Flared tip 250 can thereby engage balloon 210 in a non-axial manner, e.g., the force of flared tip 250 generated against balloon 210 can be directed radially inward. In examples, conical rim 254 can have shaping or curvature to more closely match the shape of balloon 210. In examples, conical rim 254 can have a parabolic or elliptical curvature. Thus, conical rim 254 can prevent invagination of tip 106 of flexible elongate shaft 102 during recovery of balloon 210. Second, conical rim 254 can prevent guide catheter 100 from being inserted into flow modifying device 202, particularly restriction portion 208, as can be seen in FIG. 7D. In examples, flared tip 250 can stop guide catheter 100 from the center of restriction portion 208 at length La, which can be approximately 1.5 to 2.5 millimeters. The shape and position of flared tip 250 can be selected to match curvature and shape of restriction portion 208 such that the outer surface of flared tip 250 can mate against the surface of restriction portion 208, thereby providing frictional engagement and distributing force.

FIG. 7C is a perspective view of distal portion 110 of guide catheter 100 of FIG. 7A projecting from containment sheath 258. Containment sheath 258 can comprise a tubular body having internal lumen 259 for receiving flexible elongate shaft 102. Internal lumen 259 can have a diameter that is sized to receive flexible elongate shaft 102. In examples, internal lumen 259 can be sized to allow flexible elongate shaft 102 to freely slide therein. In examples, internal lumen 259 can be lined with PTFE. Containment sheath 258 can be used to deflect conical rim 254 to a reduced-diameter state to facilitate passage through anatomy, such as by preventing prolapse of conical rim 254 and reducing the size of conical rim 254. In examples, the outer diameter of containment sheath 258 can be approximately 10 French for use with an embodiment of guide catheter 100 having diameter D1 of 9 French.

FIG. 8A is a perspective view of distal portion 110 of guide catheter 100 of the present disclosure comprising prolapse tip 260. FIG. 8B is a side view of distal portion 110 of FIG. 8A showing prolapse tip 260. FIGS. 8A and 8B are discussed concurrently.

Prolapse tip 260 can comprise an extension of tip 106 of FIGS. 1A-2. In other examples, prolapse tip 260 can comprise an attachment to guide catheter 100. Prolapse tip 260 can comprise annular rim 262, conical rim 264 and curved portion 266. Conical rim 264 can be spaced from annular rim 262 to form space 268. Prolapse tip 260 can extend from flexible elongate shaft 102 relative to central longitudinal axis CL at angle A6. Prolapse tip 260 can have axial length L7, which is the distance covered relative to central longitudinal axis CL. Prolapse tip 260 can have outer diameter D5.

Prolapse tip 260 can be pre-formed or predisposed to the shape shown in FIGS. 8A-8C. The shape of prolapse tip 260 can be configured to correspond to a corresponding shape on a medical device to be deployed with guide catheter 100. In examples, prolapse tip 260 can be shaped to conform to the shape of one or both of outflow portion 206 and inflow portion 204 of flow modifying device 202. Angle A6 can be selected to generally conform to the shape of inflow portion 204 and outflow portion 206. In examples, conical rim 264 can have shaping or curvature to more closely match the shape of inflow portion 204 and outflow portion 206. In examples, conical rim 264 can have a parabolic or elliptical curvature.

Figure 8D:
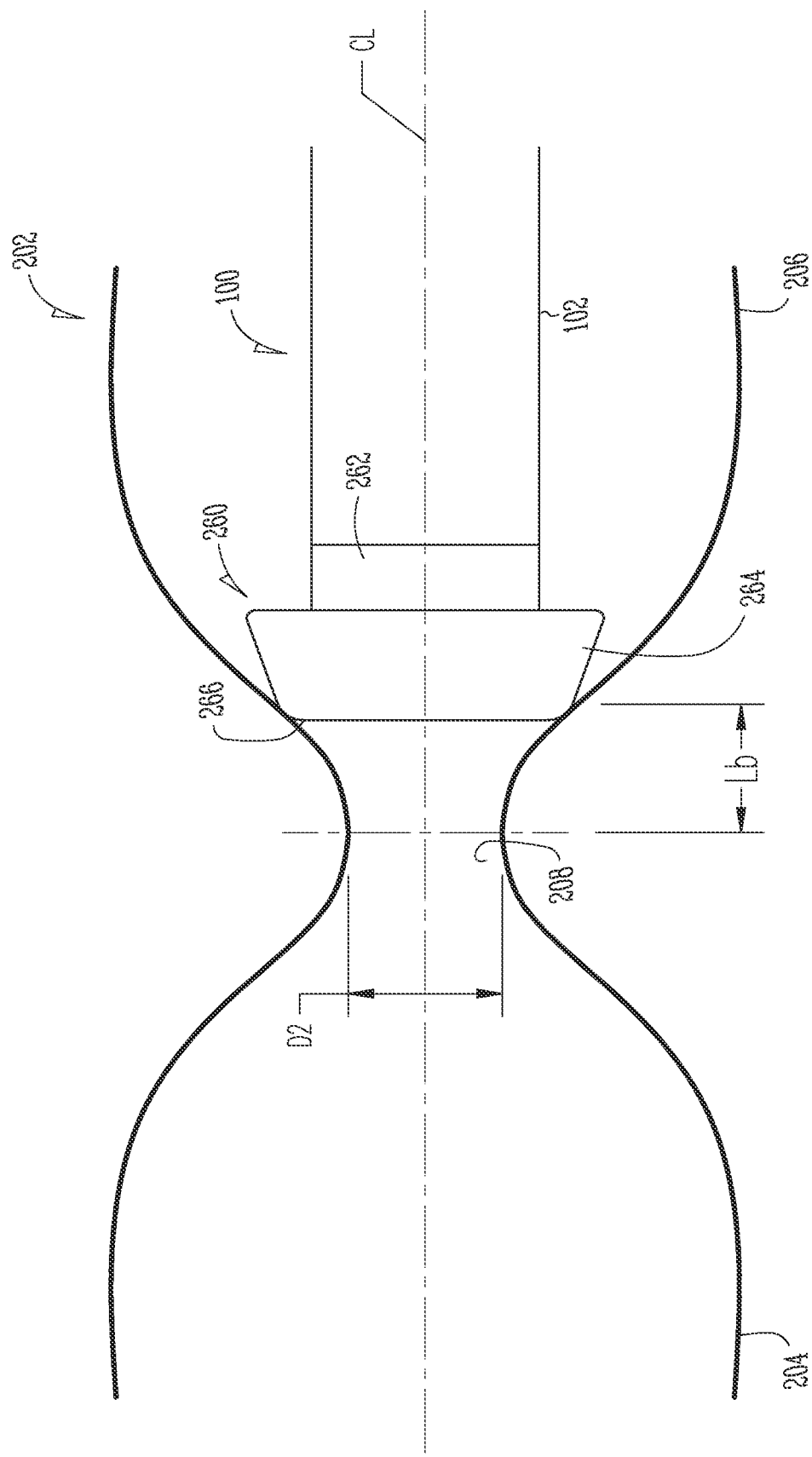
FIG. 8D is a side view of the prolapse tip of the guide catheter of FIGS. 8A-8C engaged with a flow modifying device.

In examples, outer diameter D5 of prolapse tip 260 can be selected to be approximately 0.25 mm to approximately 5 mm larger than diameter D1. In examples, angle A6, can be in the range of approximately fifteen degrees to approximately forty-five degrees. Diameter D5 can be approximately 0.25 mm to 0.5 mm larger than diameter D2 of restriction portion 208 of flow modifying device 202, which can allow for guide catheter 100 to be used to hold restriction portion 208 of flow modifying device 202 in place while withdrawing balloon 210, as shown in FIG. 8D. In examples, Length L7 can be approximately 0.5 mm to approximately 1.5 mm. Angle A6 and length L7 can be varied to achieve the desired value of diameter D5.

The shape of prolapse tip 260 can be set thermally via activating the crystalline microstructure of a polymer material forming prolapse tip 260. In examples, prolapse tip 260 can be reinforced with another material to provide the prolapse shape, such as one or more strands or a tube of Nitinol (nickel titanium) braiding.

Thus, as discussed with reference to FIG. 5B, prolapse tip 260 can be sized and shaped to provide at least two functions. First, prolapse tip 260 can allow balloon 210 (FIG. 5A) to be guided back into flexible elongate shaft 102. For example, curved portion 266 can be shaped, e.g., curved or rounded, to engage balloon 210 in a non-binding manner, such as by avoiding point contact, to urge balloon 210 back into guide catheter 100. Prolapse tip 260 can thereby engage balloon 210 in a non-axial manner, e.g., the force of prolapse tip 260 generated against balloon 210 can be directed radially inward. The presence of conical rim 264 around annular rim 262 can reinforce flexible elongate shaft 102, thereby preventing invagination of tip 106 of flexible elongate shaft 102 during recovery of balloon 210. Second, conical rim 264 can prevent guide catheter 100 from being inserted into flow modifying device 202, particularly restriction portion 208, as shown in FIG. 8D. In examples, prolapse tip 260 can stop guide catheter 100 from the center of restriction portion 208 at length Lb, which can be approximately 1.5 to 2.5 millimeters. The shape and position of prolapse tip 260 can be selected to match curvature and shape of restriction portion 208 such that the outer surface of prolapse tip 260 can mate against the surface of restriction portion 208, thereby providing frictional engagement and distributing force.

Prolapse tip 260 could be used with containment sheath 258 of 7C. Containment sheath 258 can be used to deflect conical rim 264 to an axially straightened position aligned with flexible elongate shaft 102 to facilitate passage through anatomy, such as by preventing conical rim 264 from engaging tissue and reducing the size of conical rim 264. In examples, the outer diameter of containment sheath 258 can be approximately 10 French for use with an embodiment of guide catheter 100 having diameter D1 of 9 French.

In examples, tip 106 can be configured to prolapse upon insertion into an annular body, such as an anatomic duct, another catheter or insertion device or an implantable device. As such, curved portion 266 can be replaced by a bendable portion that is pre-curved or predisposed to an axial shape where conical rim 264 axially aligns with flexible elongate shaft 102. Thus, when flexible elongate shaft 102 is pushed forward, friction generated between conical rim 264 and the surrounding annular duct can cause conical rim 264 to flip from being axially aligned with flexible elongate shaft 102 to the position illustrated. In such examples, a portion of conical rim 264 can be necked-down or thinned or made of a low durometer (e.g., flexible) material where curved portion 266 is located. Where prolapse tip 260 is configured to flex to the prolapsed shape upon insertion, the need for an insertion catheter, such as containment sheath 258 of FIG. 7C can be omitted.

FIG. 9A is a perspective view of distal portion 110 of guide catheter 100 of the present disclosure comprising balloon tip 270. FIG. 9B is a side view of distal portion 110 of FIG. 9A showing balloon tip 270. FIG. 9C is a side cross-sectional view of guide catheter 100 of FIG. 9B showing internal chamber 276 of balloon tip 270. FIGS. 9A-9C are discussed concurrently.

Balloon tip 270 can comprise an extension of tip 106 of FIGS. 1A-2. Balloon tip 270 can comprise annular rim 272 and bulbous body 274. Balloon tip 270 can comprise internal chamber 276, which can be fluidly connected to passage 278 extending through flexible elongate shaft 102. Balloon tip 270 can have axial length L8, which is the distance covered relative to central longitudinal axis CL. Balloon tip 270 can have outer diameter D6.

Figure 9D:
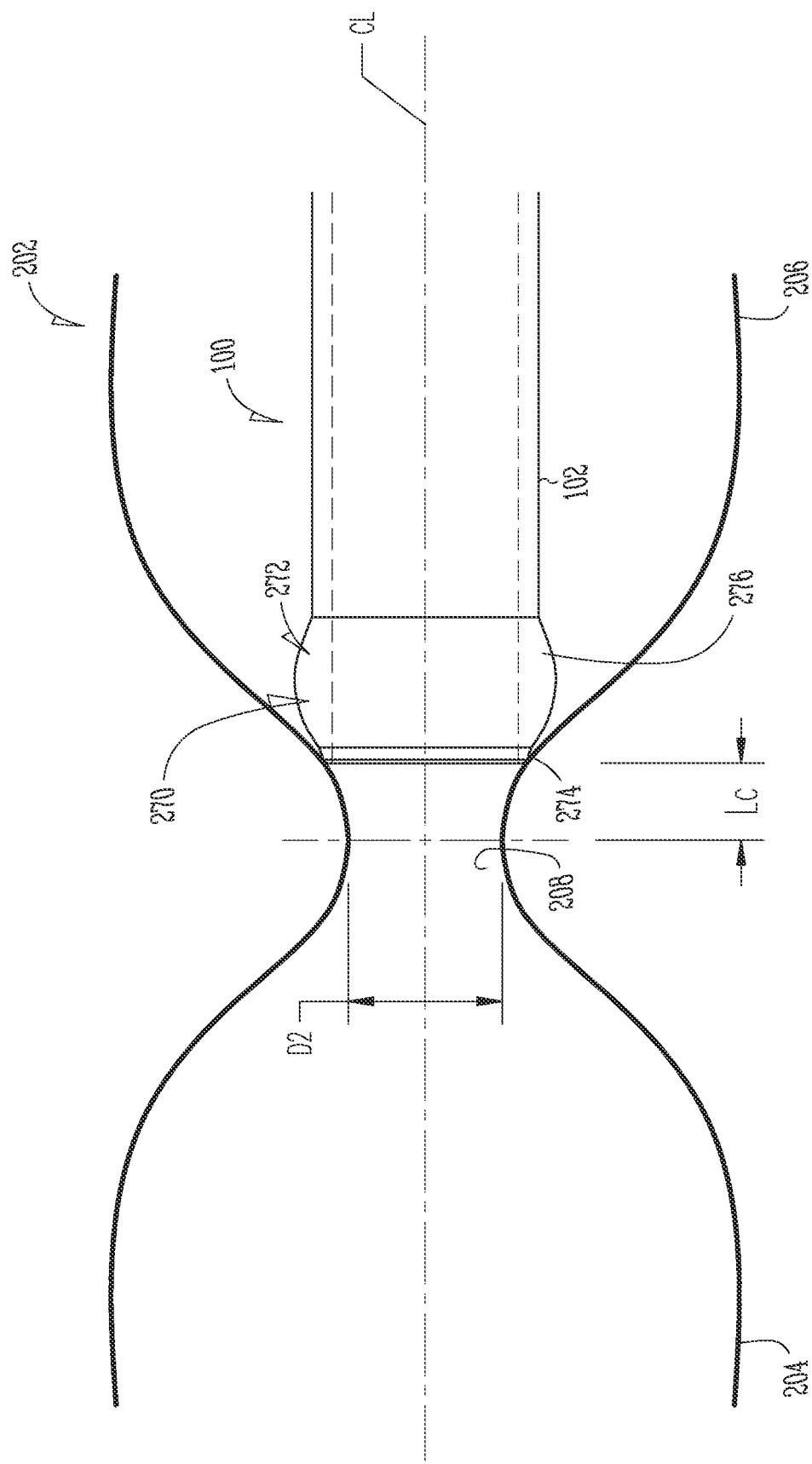
FIG. 9D is a side view of the balloon tip of the guide catheter of FIGS. 9A-9C engaged with a flow modifying device.

Balloon tip 270 can be configured to allow for easy passage through anatomy, such as by having a diameter that does not exceed diameter D1, in a first configuration, and to prevent prolapse and impaction of tip 106 in a second configuration, such as by having a diameter that exceeds diameter D2 (FIG. 5B) to hold flow modifying device 202 in place while withdrawing balloon 210, as shown in FIG. 9D. In examples, in a first configuration balloon tip 270 can be collapsed and internal chamber 276 can be deflated so that diameter D6 equal to diameter D1 and in a second configuration balloon tip 270 can be expanded and internal chamber 276 can be inflated so that diameter D6 is greater than diameter D2 of restriction portion 208 of flow modifying device 202, as shown in FIG. 9D. In examples, balloon tip 270 can stop guide catheter 100 from the center of restriction portion 208 at length Lc, which can be approximately 1.5 to 2.5 millimeters. The curvature of balloon tip 270 can be selected to match curvature and shape of restriction portion 208 such that the outer surface of balloon tip 270 can mate against the surface of restriction portion 208, thereby providing frictional engagement and distributing force. Passage 278 can extend from chamber 276 proximally and can be configured to connect to a source of pressurized gas or air. In examples, passage 278 can extend through flexible elongate shaft 102 and connect to a port on fitting 104 than can connect to the source of pressurized gas or air.

FIG. 10 is a side view of distal portion 110 of guide catheter 100 of the present disclosure comprising funnel tip 290. Funnel tip 290 can comprise conical body 292 having length L9 and major diameter D7. Diameter D7 can be selected to be approximately 0.25 mm to 0.5 mm greater than restriction portion 208 of flow modifying device 202 to hold flow modifying device 202 in place while withdrawing balloon 210. Funnel tip 290 can be similar to flared tip 250 of FIGS. 7A and 7B except funnel tip 290 can extend over a longer axial length. Whereas length L6 of flared tip 250 is generally 5 mm or less, length L9 can be in the range of approximately 10 mm to approximately 20 mm. Conical body 292 can additionally include curvature to conform with shapes of flow modifying device 202. Conical body 292 can be made of flexible material to facilitate navigation or can be rigidized to prevent invagination.

Figure 11:
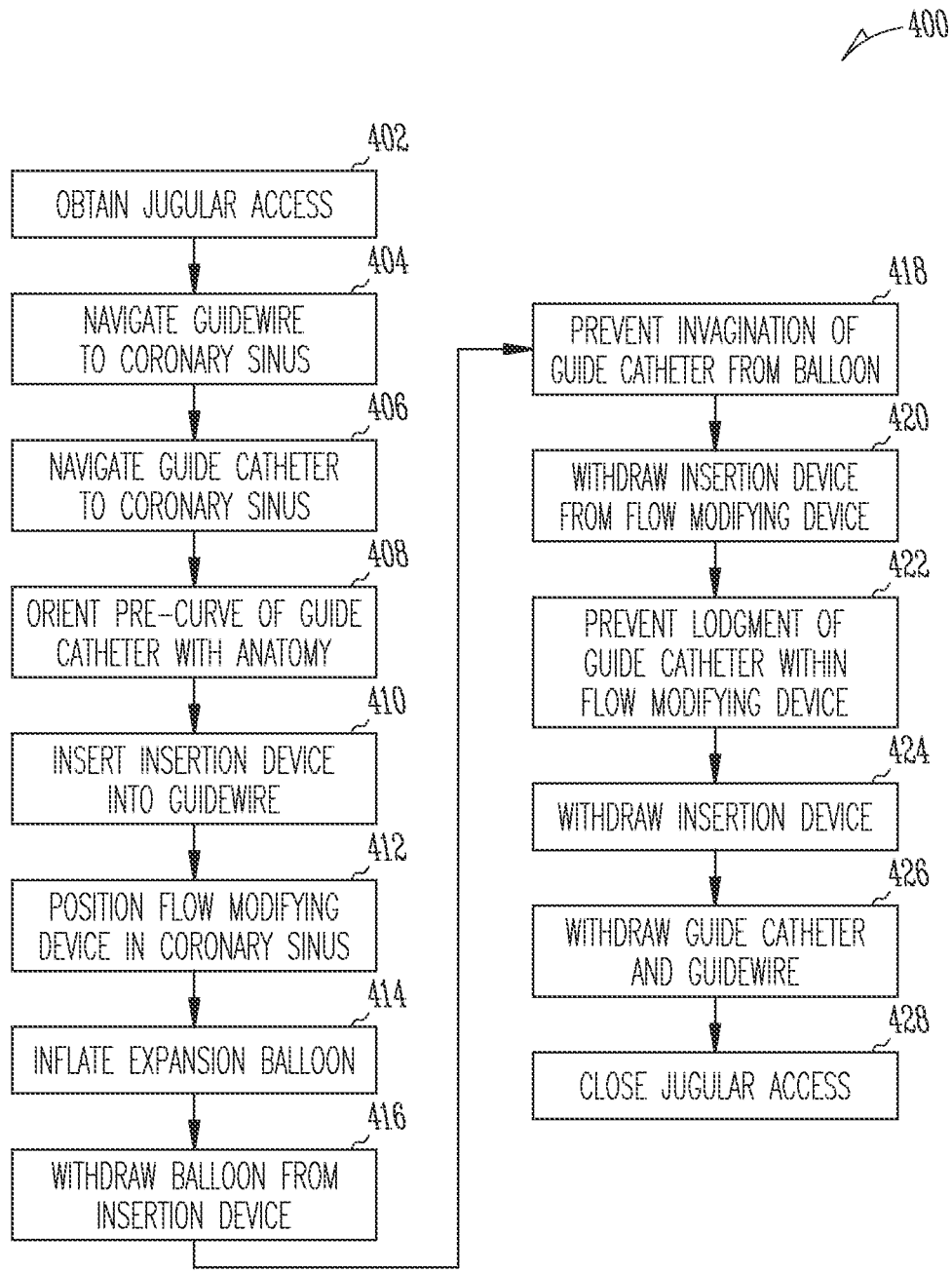
FIG. 11 is a line diagram illustrating operations of methods of implanting a flow modifying device according to the present disclosure.

FIG. 11 is a line diagram illustrating operations of method 400 of implanting flow modifying device 202 according to the present disclosure. Method 400 illustrates a particular sequence of operations. However, not all operations need to be performed in all methods of the present disclosure. Additionally, some operations can be performed in different sequences. Method 400 is described with reference to implanting a flow modifying device in a coronary sinus of a heart via jugular access. However, other procedures can be performed using the devices and methods described herein.

At operation 402, access to the heart can be opened in a patient. In examples, access to the heart can be obtained via a jugular artery. In additional examples, access to the heart can be obtained via a femoral artery.

At operation 404, a guidewire, such as guidewire 213, can be navigated through the anatomy to reach a target area within the heart. In examples, the guidewire can be inserted using a multipurpose catheter that can be steered and/or navigated. In examples, the target area can be the coronary sinus. The guide wire can be navigated through a jugular vein, such as left external jugular vein 171LE (FIG. 4A), through superior vena cava 172S (FIG. 4B), through coronary sinus ostium 177, and into coronary sinus 176.

At operation 406, a guide catheter, such as guide catheter 100, can be navigated through the anatomy to reach the target area. The guide catheter can be slid over the guidewire used in operation 404. In other examples, use of a guidewire can be omitted. Guide catheter 100 can be inserted such that tip 106 is positioned within coronary sinus 176.

At operation 408, the guide catheter can be oriented with the anatomic pathway to the target area. Specifically, guide catheter 100 can be oriented such that pre-curvature of distal portion 110 tracks with the shape of the anatomic pathway of the access route. For example, pre-curvature matching the shape of the superior vena cava and coronary sinus can be oriented to extend along the superior vena cava and coronary sinus. As such, stresses and strains within guide catheter 110 from being bent against the pre-curvature can be relieved. In examples, indicia on guide catheter 100 can be referenced to align the pre-curvature with the anatomy. For example, indicia, such as indicia 186 (FIG. 6B), can be read visually or felt tactilely to facilitate proper orientation of the pre-curvature. In examples, the pre-curvature of pre-curved guide catheter 100 can be oriented to by aligning indicia on pre-curved guide catheter 100 to face in a direction that the pre-curvature of pre-curved guide catheter 100 is desired to extend. The indicia can also be aligned into a plane in which the pre-curvature of pre-curved guide catheter 100 is pre-disposed to extend into.

At operation 410, an insertion device can be inserted into the guide catheter to position an anatomic implant at the target area. For example, balloon catheter 200 (FIGS. 4B and 6A) can be inserted into guide catheter 100. In examples, operation 410 can be performed simultaneously with operation 406. Balloon catheter 200 can be inserted into coronary sinus 176 such that flow modifying device 202 is positioned within coronary sinus 176 in a collapsed or non-deployed state.

At operation 412, an anatomic implant, such as flow modifying device 202 (FIG. 6A) can be positioned in the target area using the insertion instrument. In examples, the flow modifying device can be used to treat angina. Guide catheter 100 can be retracted from balloon catheter 200 to expose flow modifying device 202.

At operation 414, flow modifying device 202 can be expanded to conform to the desired anatomic feature. In examples, flow modifying device 202 can be expanded to conform to a coronary sinus. In examples, balloon 210 can be expanded via the use of pressurized gas or air. Positioning and size of flow modifying device 202 can be verified using contrast dye injected through guide catheter 100.

At operation 416, the expansion device used to expand flow modifying device 202 can be collapsed and withdrawn from flow modifying device 202. Balloon 210 can be deflated, such as by discontinuing the application of pressurized gas or air. Balloon catheter 200 can be pulled proximally away from flow modifying device 202 into guide catheter 100.

At operation 418, balloon 210 can be prevented from invaginating guide catheter 100 using any of the features described herein. For example, an enlarged or strengthen tip 106 can be used to prevent invagination. Enlarged tips, such as flared tip 250 (FIG. 7A) and funnel tip 290 (FIG. 10), can have an enlarged diameter to allow balloon 210 to enter guide catheter 100 without pushing on the distal-most end of guide catheter 100. Enlarged tips, such as prolapse tip 260 (FIG. 8A), can provide strengthening to tip 106 to resist invagination. Enlarged tips, such as balloon tip 270 (FIG. 9A), can be expanded, such as via inflation, to overcome invagination or to resist the tendency to invaginate.

At operation 420, the insertion device can be withdrawn from the flow modifying device. For example, balloon catheter 200 can be withdrawn from flow modifying device 202 after the proximal-most portion of balloon 210 is within guide catheter 100. Withdrawing the insertion device can involve retracting the insertion device into the guide catheter, which can cause the guide catheter to advance forward.

At operation 422, the guide catheter can be prevented from lodging within the flow modifying device. In particular, guide catheter 100 can be prevented from lodging within restriction portion 208 of flow modifying device 202. For example, the enlarged tips of guide catheter 100 described herein can prevent guide catheter 100 from entering restriction portion 208. Enlarged tips, such as flared tip 250 (FIG. 7A) and funnel tip 290 (FIG. 10), can have an enlarged diameter to prevent tip 106 from entering restriction portion 208. Enlarged tips, such as prolapse tip 260 (FIG. 8A), can be shaped to push against restriction portion 208 and prevent entry therein. Enlarged tips, such as balloon tip 270 (FIG. 9A), can be expanded, such as via inflation, to prevent entry of tip 106 into restriction portion 208.

At operation 424, the insertion device can be withdrawn from the patient. For example, balloon catheter 200 can be withdrawn from guide catheter 100.

At operation 426, the guide catheter and guidewire can be withdrawn from the patient. Guide catheter 100 can be withdrawn from the jugular simultaneously with or alternatively to guide wire 213.

At operation 428, the access point in the patient can be closed, leaving the implanted medical device within the anatomy.

Examples

Example 1 is a guide catheter for cannulating a coronary sinus from a superior vena cava, the guide catheter comprising: a flexible elongate shaft comprising: a proximal portion; a pre-formed distal portion comprising: a proximal straight zone; a proximal curved zone extending along a first curved path from the proximal straight zone; a distal straight zone extending along a straight path from the proximal curved zone; and a distal curved zone extending along a second curved path from the distal straight zone; and a distal tip extending from the distal curved zone.

In Example 2, the subject matter of Example 1 optionally includes wherein the pre-formed distal portion of the flexible elongate shaft has a size and a shape selected such that the pre-formed distal portion of the flexible elongate shaft is supported on a wall of the superior vena cava when locating an ostium of the coronary sinus with the distal tip.

In Example 3, the subject matter of any one or more of Examples 1-2 optionally include wherein the proximal curved zone has a variable radius of curvature.

In Example 4, the subject matter of Example 3 optionally includes wherein the proximal curved zone comprises: a first segment; and a second segment.

In Example 5, the subject matter of any one or more of Examples 3-4 optionally include where in the proximal curved zone comprises a first segment extending from the proximal straight zone along a first curved trajectory having a radius of curvature of approximately seven-hundred-ninety-four millimeters plus or minus five millimeters.

In Example 6, the subject matter of any one or more of Examples 4-5 optionally include where in the proximal curved zone comprises a second segment extending from the first segment along a second curved trajectory having a radius curvature of approximately two-hundred-nineteen millimeters plus or minus five millimeters.

In Example 7, the subject matter of any one or more of Examples 1-6 optionally include a distal straight zone having a length of approximately 32.5 millimeters plus or minus five millimeters.

In Example 8, the subject matter of any one or more of Examples 1-7 optionally include where in the distal curved zone has a variable radius of curvature.

In Example 9, the subject matter of Example 8 optionally includes wherein the distal curved zone comprises: a first segment; a second segment; a third segment; a fourth segment; and a fifth segment.

In Example 10, the subject matter of any one or more of Examples 8-9 optionally include wherein the distal curved zone comprises a first segment extending from the distal straight zone along a first curved trajectory having a radius of curvature of approximately seventy-one millimeters plus or minus five millimeters.

In Example 11, the subject matter of Example 10 optionally includes wherein the distal curved zone comprises a second segment extending from the first segment along a second curved trajectory having a radius of curvature of approximately twenty-six millimeters plus or minus five millimeters.

In Example 12, the subject matter of Example 11 optionally includes wherein the distal curved zone comprises a third segment extending from the second segment along a third curved trajectory having a radius of curvature of approximately thirty-six millimeters plus or minus five millimeters.

In Example 13, the subject matter of Example 12 optionally includes wherein the distal curved zone comprises a fourth segment extending from the third segment along a fourth curved trajectory having a radius of curvature of approximately sixty-eight millimeters plus or minus five millimeters.

In Example 14, the subject matter of Example 13 optionally includes wherein the distal curved zone comprises a fifth segment extending from the fourth segment along a fifth curved trajectory having a radius of curvature of approximately one-hundred-twenty-six millimeters plus or minus five millimeters.

In Example 15, the subject matter of any one or more of Examples 1-14 optionally include wherein the pre-formed distal portion comprises a plurality of stiffness sections, each of the plurality of stiffness sections having a different level of flexibility.

In Example 16, the subject matter of Example 15 optionally includes the plurality of stiffness sections comprises a first stiffness section having a first tip that extends along a trajectory forming a first angle with the proximal straight zone of approximately ten degrees plus or minus 0.5 degrees.

In Example 17, the subject matter of Example 16 optionally includes the first stiffness section comprises a length of approximately four-hundred-eighty-five millimeters and has a durometer of approximately 72 D plus or minus 5 D.

In Example 18, the subject matter of any one or more of Examples 16-17 optionally include the plurality of stiffness sections comprises a second stiffness section having a second tip that extends along a trajectory forming a second angle with the proximal straight zone of approximately twenty-eight degrees plus or minus 0.5 degrees.

In Example 19, the subject matter of Example 18 optionally includes the second stiffness section comprises a length of approximately fifty millimeters and has a durometer of approximately 63 D plus or minus 5 D.

In Example 20, the subject matter of any one or more of Examples 18-19 optionally include the plurality of stiffness sections comprises a third stiffness section having a third tip that extends along a trajectory forming a third angle with the proximal straight zone of approximately eighty-seven degrees plus or minus 0.5 degrees.

In Example 21, the subject matter of Example 20 optionally includes the third stiffness section comprises a length of approximately thirty-five millimeters and has a durometer of approximately 55 D plus or minus 5 D.

In Example 22, the subject matter of any one or more of Examples 20-21 optionally include the plurality of stiffness sections comprises a fourth stiffness section having a fourth tip that extends along a trajectory forming a fourth angle with the proximal straight zone of approximately sixty-two degrees plus or minus 0.5 degrees.

In Example 23, the subject matter of Example 22 optionally includes the fourth stiffness section comprises a length of approximately thirty-eight millimeters and has a durometer of approximately 35 D plus or minus 5 D.

In Example 24, the subject matter of any one or more of Examples 15-23 optionally include the distal tip comprises a length of approximately two millimeters and has a durometer of approximately 25 D plus or minus 5 D.

In Example 25, the subject matter of any one or more of Examples 1-24 optionally include a fitting connected to a proximal end of the proximal portion, the fitting including indicia indicating a plane of curvature of the pre-formed distal portion.

In Example 26, the subject matter of Example 25 optionally includes wherein the indicia comprises a protrusion illustrating a direction of pre-curvature of the pre-formed distal portion, the protrusion comprising an elongate body curved in a direction the pre-formed distal portion is curved.

Example 27 is a guide catheter for delivering an expandable flow modifying apparatus to a heart passage, the guide catheter comprising: a flexible elongate shaft comprising: a proximal portion comprising a fitting for receiving an insertion instrument; and distal portion comprising a distal tip, wherein the distal tip comprises an enlarged tip to prevent the flexible elongate shaft from passing through the expandable flow modifying apparatus.

In Example 28, the subject matter of Example 27 optionally includes the flexible elongate shaft has a diameter of approximately 3.0 millimeters.

In Example 29, the subject matter of any one or more of Examples 27-28 optionally include wherein the enlarged tip comprises a flared tip.

In Example 30, the subject matter of any one or more of Examples 28-29 optionally include the flared tip extends approximately 2 millimeters in length and has a maximum diameter of approximately 3.3 millimeters.

In Example 31, the subject matter of any one or more of Examples 27-30 optionally include wherein the enlarged tip comprises a funnel tip.

In Example 32, the subject matter of Example 31 optionally includes the funnel tip extends approximately 10 millimeters to approximately 20 millimeters in length and has a maximum diameter of approximately 3.3 millimeters.

In Example 33, the subject matter of any one or more of Examples 28-32 optionally include wherein the enlarged tip comprises a prolapse tip.

In Example 34, the subject matter of Example 33 optionally includes wherein the prolapse tip comprises a length of the flexible elongate shaft folded radially outward over the flexible elongate shaft.

In Example 35, the subject matter of Example 34 optionally includes wherein the length of the flexible elongate shaft folded radially outward forms an oblique angle with a central axis of the flexible elongate shaft.

In Example 36, the subject matter of any one or more of Examples 34-35 optionally include wherein the prolapse tip can be straightened to align with the flexible elongate shaft and can be constricted to contact the flexible elongate shaft.

In Example 37, the subject matter of any one or more of Examples 27-36 optionally include wherein the enlarged tip comprises a balloon tip.

In Example 38, the subject matter of Example 37 optionally includes wherein the balloon tip comprises a length of the flexible elongate shaft that is inflatable.

In Example 39, the subject matter of Example 38 optionally includes wherein the flexible elongate shaft comprises a fluid passage extending internally through at least a portion of the flexible elongate shaft to connect to an airspace within the balloon tip.

In Example 40, the subject matter of any one or more of Examples 28-39 optionally include a containment sheath slidable along the flexible elongate shaft to collapse the enlarged tip.

Example 41 is a method of retrieving a balloon catheter from a deployed medical device, the method comprising: extending a delivery device from a guide catheter; positioning a flow modifying device with the delivery device; expanding the flow modifying device with a balloon connected to the delivery device; deflating the balloon; pulling the delivery device proximally into the guide catheter to move the balloon away from the flow modifying device; and preventing the guide catheter from becoming lodged within the flow modifying device with an enlarged distal tip of the guide catheter.

In Example 42, the subject matter of Example 41 optionally includes wherein preventing the guide catheter from becoming lodged within the flow modifying device with the enlarged distal tip of the guide catheter comprises: engaging a flared tip defining the enlarged distal tip with a constriction portion of the flow modifying device.

In Example 43, the subject matter of Example 42 optionally includes collapsing the flared tip with a containment sheath during insertion of the guide catheter.

In Example 44, the subject matter of any one or more of Examples 41-43 optionally include wherein preventing the guide catheter from becoming lodged within the flow modifying device with the enlarged distal tip of the guide catheter comprises: engaging a funnel tip defining the enlarged distal tip with a constriction portion of the flow modifying device.

In Example 45, the subject matter of Example 44 optionally includes wherein a length of the funnel tip is greater than a diameter of the guide catheter.

In Example 46, the subject matter of any one or more of Examples 41-45 optionally include wherein preventing the guide catheter from becoming lodged within the flow modifying device with the enlarged distal tip of the guide catheter comprises: engaging a prolapse tip defining the enlarged distal tip with a constriction portion of the flow modifying device.

In Example 47, the subject matter of Example 46 optionally includes forming the prolapse tip by frictionally engaging the guide catheter with a surrounding surface to induce formation of the prolapse tip.

In Example 48, the subject matter of any one or more of Examples 41-47 optionally include wherein preventing the guide catheter from becoming lodged within the flow modifying device with the enlarged distal tip of the guide catheter comprises: engaging a balloon tip defining the enlarged distal tip with a constriction portion of the flow modifying device.

In Example 49, the subject matter of Example 48 optionally includes temporarily inflating the balloon tip before engaging the balloon tip with the constriction portion of the flow modifying device.

In Example 50, the subject matter of any one or more of Examples 41-49 optionally include preventing the balloon from collapsing the guide catheter with the enlarged distal tip.

In Example 51, the subject matter of Example 50 optionally includes wherein preventing the balloon from collapsing the guide catheter with the enlarged distal tip comprises: guiding the balloon into the guide catheter with a flared tip defining the enlarged distal tip.

In Example 52, the subject matter of any one or more of Examples 50-51 optionally include wherein preventing the balloon from collapsing the guide catheter with the enlarged distal tip comprises: guiding the balloon into the guide catheter with a funnel tip defining the enlarged distal tip.

In Example 53, the subject matter of any one or more of Examples 50-52 optionally include wherein preventing the balloon from collapsing the guide catheter with the enlarged distal tip comprises: strengthening the guide catheter with a prolapse tip defining the enlarged distal tip.

In Example 54, the subject matter of any one or more of Examples 50-53 optionally include wherein preventing the balloon from collapsing the guide catheter with the enlarged distal tip comprises: strengthening the guide catheter with a balloon tip defining the enlarged distal tip.

Example 55 is a method of inserting a pre-curved guide catheter into an anatomic passageway, the method comprising: inserting the pre-curved guide catheter into the anatomic passageway; and orienting pre-curvature of the pre-curved guide catheter matches a shape of the anatomic passageway.

In Example 56, the subject matter of Example 55 optionally includes wherein orienting pre-curvature of the pre-curved guide catheter matches a shape of the anatomic passageway comprises aligning indicia on the pre-curved guide catheter to face in a direction that the pre-curvature of the pre-curved guide catheter is desired to extend.

In Example 57, the subject matter of Example 56 optionally includes wherein aligning indicia on the pre-curved guide catheter to face in a direction that the pre-curvature of the pre-curved guide catheter is desired to extend comprises orienting the indicia into a plane in which the pre-curvature of the pre-curved guide catheter is predisposed to extend into.

In Example 58, the subject matter of any one or more of Examples 55-57 optionally include wherein inserting the pre-curved guide catheter into the anatomic passageway comprises: positioning a proximal straight zone of the pre-curvature in a superior vena cava of a heart; positioning a proximal curved zone of the pre-curvature proximate an exit of the superior vena cava of a heart; positioning a distal straight zone of the pre-curvature in a right atrium of the heart; and positioning a distal curved zone of the pre-curvature in a coronary sinus of the heart.

In Example 59, the subject matter of Example 58 optionally includes wherein the proximal curved zone comprises two segments with different curvature.

In Example 60, the subject matter of any one or more of Examples 58-59 optionally include wherein the distal curved zone comprises five segments with different curvature.

Example 61 is a system for implanting a flow modifying device in vasculature of a heart, the system comprising: a flow modifying device comprising: a tubular body comprising: a first opening located at a first end of the tubular body; a second opening located at a second end of the tubular body; and a neck positioned between the first opening and the second opening; and a guide catheter comprising: a flexible elongate shaft comprising: a proximal portion comprising a fitting for receiving an insertion instrument; and distal portion comprising a distal tip, wherein the distal tip comprises an enlarged tip to prevent the flexible elongate shaft from passing through the flow modifying device.

In Example 62, the subject matter of Example 61 optionally includes wherein: the tubular body is configured to expand from a first configuration wherein the first opening, second opening and neck have a first diameter to a second configuration wherein the first opening, second opening and neck are larger than the first diameter.

In Example 63, the subject matter of Example 62 optionally includes wherein the distal portion of the flexible elongate shaft is sized smaller than the neck in the second configuration and the enlarged tip of the distal portion is sized larger than the neck in the second configuration.

In Example 64, the subject matter of any one or more of Examples 62-63 optionally include wherein the tubular body is increases in diameter from the neck to the first opening and the second opening and the enlarged tip is shaped to conform to a shape of the tubular body between the neck and one of the first opening and the second opening.

In Example 65, the subject matter of any one or more of Examples 62-64 optionally include wherein, in the second configuration, the tubular body comprises: the first opening; a first flared section extending from the first opening; the neck; a second flared section extending from the neck; and the second opening.

In Example 66, the subject matter of Example 65 optionally includes wherein the tubular body further comprises in the second configuration: a first conical section positioned between the first opening and the first flared section; and a second conical section positioned between the second opening and the second flared section.

In Example 67, the subject matter of any one or more of Examples 65-66 optionally include wherein the neck comprises a curved portion of the tubular body in the second configuration.

In Example 68, the subject matter of any one or more of Examples 65-67 optionally include wherein the enlarged tip is shaped to conform to the first or second flared portion.

In Example 69, the subject matter of any one or more of Examples 61-68 optionally include wherein the enlarged tip comprises a flared tip.

In Example 70, the subject matter of any one or more of Examples 61-69 optionally include wherein the enlarged tip comprises a funnel tip.

In Example 71, the subject matter of any one or more of Examples 61-70 optionally include wherein the enlarged tip comprises a prolapse tip.

In Example 72, the subject matter of any one or more of Examples 61-71 optionally include wherein the enlarged tip comprises a balloon tip.

In Example 73, the subject matter of any one or more of Examples 61-72 optionally include a containment sheath slidable along the flexible elongate shaft to collapse the enlarged tip.

In Example 74, the subject matter of any one or more of Examples 61-73 optionally include a balloon catheter comprising an elongate shaft and an inflatable balloon configured to be inserted into the tubular body of the flow modifying device in a collapsed state, the inflatable balloon comprising a first end configured to expand the first opening of the tubular body and a second end configured to expand the second opening of the tubular body, wherein at least one of the first end and the second end of the inflatable balloon is configured to engage the enlarged tip of the guide catheter to urge the inflatable balloon back into the guide catheter in a deflated state.

In Example 75, the subject matter of any one or more of Examples 61-74 optionally include the enlarged tip of the guide catheter being configured to engage the inflatable balloon in a non-axial direction.

In Example 76, the subject matter of any one or more of Examples 61-75 optionally include the enlarged tip of the guide catheter comprising a conical wall disposed at an angel relative to the flexible elongate shaft of the guide catheter to be tangent to the first or second end of the inflatable balloon in an inflated state.

In Example 77, the subject matter of any one or more of Examples 61-75 optionally include the enlarged tip of the guide catheter comprises a rounded leading edge configured to engage the first or second end of the inflatable balloon over an arcuate contact area.

In Example 78, the subject matter of any one or more of Examples 61-77 optionally include the enlarged tip of the guide catheter is configured to reinforce the guide catheter to resist inward forces generated by the inflatable balloon being pulled into the guide catheter in a deflated state tending to invaginate the guide catheter.

Each of these non-limiting examples can stand on its own, or can be combined in various permutations or combinations with one or more of the other examples.

VARIOUS NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A system for implanting a flow modifying device in vasculature of a heart, the system comprising:
a flow modifying device comprising:
a tubular body comprising:
a first opening located at a proximal end of the tubular body;
a second opening located at a distal end of the tubular body; and
a neck positioned between the first opening and the second opening, wherein the tubular body is configured to expand from a first configuration to a second configuration, wherein in the second configuration the first opening comprises a first diameter and the neck comprises a second diameter smaller than the first diameter; and
a guide catheter comprising:
a flexible elongate shaft comprising:
a proximal portion comprising a fitting for receiving an insertion instrument; and
a distal portion comprising a distal tip configured to be receivable by the first opening of the tubular body when the tubular body is in the second configuration, wherein the distal tip comprises an enlarged tip to prevent the flexible elongate shaft from passing through the neck of the flow modifying device when the tubular body is in the second configuration.

2. The system of claim 1, wherein:
when the tubular body is in the second configuration respective diameters of the first opening, second opening, and neck are larger than when the tubular body is in the first configuration.

3. The system of claim 2, wherein a section of the distal portion of the flexible elongate shaft is sized smaller than the neck in the second configuration and the enlarged tip of the distal portion is sized larger than the neck in the second configuration.

4. The system of claim 2, wherein the tubular body increases in diameter from the neck to the first opening and the second opening and the enlarged tip is shaped to conform to a shape of the tubular body between the neck and the first opening.

5. The system of claim 2, wherein, in the second configuration, the tubular body comprises:
a first flared section between the first opening and the neck; and
a second flared section between the neck and the second opening.

6. The system of claim 5, wherein the neck comprises a curved portion of the tubular body in the second configuration.

7. The system of claim 5, wherein the enlarged tip is shaped to conform to the first flared portion.

8. The system of claim 1, wherein the enlarged tip comprises a flared tip.

9. The system of claim 1, wherein the enlarged tip comprises a funnel tip.

10. The system of claim 1, wherein the enlarged tip comprises a prolapse tip.

11. The system of claim 1, wherein the enlarged tip comprises a balloon tip.

12. The system of claim 1, further comprising a containment sheath slidable along the flexible elongate shaft and configured to collapse the enlarged tip.

13. The system of claim 1, further comprising a balloon catheter comprising:
   an elongate shaft; and
   an inflatable balloon configured to be inserted into the tubular body of the flow modifying device when the tubular body is in the first configuration, the inflatable balloon comprising:
      a first end configured to expand the first opening of the tubular body; and
      a second end configured to expand the second opening of the tubular body;
   wherein the first end of the inflatable balloon is configured to engage the enlarged tip of the guide catheter to urge the inflatable balloon back into the guide catheter in a deflated state.

14. The system of claim 13, wherein the enlarged tip of the guide catheter is configured to engage the inflatable balloon in a non-axial direction.

15. The system of claim 14, wherein the enlarged tip of the guide catheter comprises a conical wall disposed at an angle relative to the flexible elongate shaft of the guide catheter to be tangent to the first end of the inflatable balloon in an inflated state.

16. The system of claim 14, wherein the enlarged tip of the guide catheter comprises a rounded leading edge configured to engage the first end of the inflatable balloon over an arcuate contact area.

17. The system of claim 13, wherein the enlarged tip of the guide catheter is configured to reinforce the guide catheter to resist inward forces generated by the inflatable balloon being pulled into the guide catheter in the deflated state tending to invaginate the guide catheter.

* * * * *